US012593969B2

(12) United States Patent
Schack et al.

(10) Patent No.: US 12,593,969 B2
(45) Date of Patent: Apr. 7, 2026

(54) 3D SCANNER SYSTEM FOR PROVIDING FEEDBACK

(71) Applicant: 3SHAPE A/S, Copenhagen K (DK)

(72) Inventors: Signe Friis Schack, Copenhagen K (DK); Astrid Anna Toftegaard, Copenhagen K (DK); Mikael Nielsen, Copenhagen K (DK); Bjørn Lindegaard, Copenhagen K (DK); Samuele Vimercati, Copenhagen K (DK)

(73) Assignee: 3Shape A/S, Kobenhavn K (DK)

( * ) Notice: Subject to any disclaimer, the term of this patent is extended or adjusted under 35 U.S.C. 154(b) by 301 days.

(21) Appl. No.: 18/503,311

(22) Filed: Nov. 7, 2023

(65) Prior Publication Data
US 2024/0148242 A1 May 9, 2024

(30) Foreign Application Priority Data

Nov. 9, 2022 (EP) ..................................... 22206300
Jul. 25, 2023 (EP) ..................................... 23187555

(51) Int. Cl.
*A61B 1/24* (2006.01)
*A61B 1/00* (2006.01)
(52) U.S. Cl.
CPC ............ *A61B 1/24* (2013.01); *A61B 1/00045* (2013.01); *A61B 1/00172* (2013.01)
(58) Field of Classification Search
None
See application file for complete search history.

(56) References Cited

U.S. PATENT DOCUMENTS

| | | | |
|---|---|---|---|
| 8,878,905 | B2 | 11/2014 | Fisker et al. |
| 9,454,846 | B2 | 9/2016 | Pesach et al. |
| 10,108,269 | B2 | 10/2018 | Sabina et al. |

(Continued)

FOREIGN PATENT DOCUMENTS

| | | |
|---|---|---|
| CN | 107427345 B | 5/2021 |
| EP | 2442720 B1 | 8/2016 |

(Continued)

OTHER PUBLICATIONS

The European Search Report issued on Mar. 1, 2024, by the European Patent Office in corresponding European Application No. 23 207 051.6. (4 pages).

*Primary Examiner* — Toan H Vu
(74) *Attorney, Agent, or Firm* — BUCHANAN INGERSOLL & ROONEY PC

(57) ABSTRACT

The present disclosure relates to a 3D scanner system for scanning the oral cavity of a patient. In particular, the disclosure relates to feedback mechanisms and user interfaces of intraoral scanners. In some embodiments, the 3D scanner system comprises an intraoral scanner comprising one or more reconfigurable buttons, wherein each reconfigurable button comprises a force sensor, such as a strain gauge sensor; and wherein the intraoral scanner further comprises a display configured for displaying one or more icons, texts, or animations, associated with the reconfigurable buttons, wherein the display covers the force sensors, and wherein the scanner system further comprises one or more processors configured to generate 3D scan data of at least a part of the dental arch.

20 Claims, 14 Drawing Sheets

(56)  References Cited

U.S. PATENT DOCUMENTS

| 10,599,227 | B2 | | 3/2020 | Sabina et al. | |
|---|---|---|---|---|---|
| 11,392,210 | B2 | | 7/2022 | Sabina et al. | |
| 11,954,262 | B2 | | 4/2024 | Sabina et al. | |
| 2013/0257718 | A1 | * | 10/2013 | Ojelund | G06F 3/011 |
| | | | | | 345/156 |
| 2019/0231492 | A1 | * | 8/2019 | Sabina | A61B 1/0638 |
| 2019/0298502 | A1 | * | 10/2019 | Szczerbaniewicz | A61C 19/04 |
| 2020/0192488 | A1 | * | 6/2020 | Sabina | A61C 13/0004 |
| 2022/0189611 | A1 | * | 6/2022 | Farkash | G06T 7/0016 |
| 2022/0233078 | A1 | | 7/2022 | Fridman et al. | |
| 2022/0233283 | A1 | | 7/2022 | Fridman et al. | |
| 2022/0233284 | A1 | * | 7/2022 | Fridman | G16H 50/50 |

FOREIGN PATENT DOCUMENTS

| EP | 3265021 | B1 | 4/2021 |
|---|---|---|---|
| EP | 4307229 | A1 | 1/2024 |
| WO | 2022164827 | A1 | 8/2022 |
| WO | 2023117981 | A1 | 6/2023 |
| WO | 2023187181 | A1 | 10/2023 |
| WO | 2024013282 | A1 | 1/2024 |

* cited by examiner

3D SCANNER SYSTEM FOR PROVIDING FEEDBACK

TECHNICAL FIELD

The present disclosure relates to a 3D scanner system for scanning the oral cavity of a patient. Furthermore, the disclosure relates to feedback mechanisms and user interfaces of intraoral scanners.

BACKGROUND

Digital dental scanning systems, both intraoral and laboratory-based, are playing an important role in transforming both restorative and orthodontic dentistry. Real-time imaging using the scanning systems allows for generating three-dimensional digital models of single or multiple teeth, whole arches which may include restorations or implants, opposition arches, occlusion, and surrounding soft tissue or even dentures for edentulous patients.

Existing 3D dental scanning systems typically feature a display connected to a computer for displaying a 3D model of the teeth to the dentist and patient. Typically, the 3D model is generated continuously during the scanning session, such that the dentist can follow the progress of the scanning session. Thus, the 3D model on the display serves as a feedback to the dentist, such that the dentist knows whether 3D scan data is acquired and if sufficient data is acquired of all of the relevant areas.

A drawback to setups involving an intraoral scanner, a computer, and a display is that the attention of the dentist tends to be on the display instead of on the patient. Another drawback is that there is typically a bit of lag between the actual movements of the scanner and the reconstruction and rendering of the 3D model on the display. Hence, if the dentist uses the latter as a feedback mechanism, it can cause difficulty of performing the scan due to this latency. Yet another drawback is that such equipment is expensive. Finally, existing dental scanning system setups are typically inflexible, since the scanner is tied to the workflow presented in the software in the display. Therefore, the user has to make sure that all components of the setup are connected and ready. Furthermore, the user has to scan in a place where such a setup is installed.

On the other hand, if the display is omitted entirely from the dental scanning system, the dentist lacks an important feedback mechanism. In this case, the dentist will not know if sufficient scan data has been acquired and what areas needs to be scanned in more detail. Thus, it is desired to find other feedback solutions that are able to provide the user with these details. It is therefore desired to develop a scanner system that is able to overcome these drawbacks.

In particular, it is desired to develop solutions that are more cost-effective and flexible, which enables the user to scan from almost anywhere, ideally without the dependency of an external display.

SUMMARY

The present disclosure addresses the above-mentioned challenges by providing a 3D scanner system for scanning a dental arch inside an oral cavity of a patient during a scanning session, wherein the scanner system comprises an intraoral scanner. The disclosure suggests a variety of different solutions to provide feedback to the user, in a scenario where the scanner system does not feature an external display as the typical systems.

When scanning a patient, oftentimes both of the dental arches of the patient are scanned, such that a digital 3D representation of the patient's teeth can be generated. In a typical scan workflow, first the lower jaw (mandible) is scanned, and then the upper jaw (maxilla) is subsequently scanned. Then the patient's natural bite is scanned; thus, the teeth of the patient are scanned when in occlusion to determine the bite. In the dental arches, a number of different dental objects may be present, such as: natural teeth, artificial teeth (crowns), missing teeth, tooth preparations, or other dental restorations. When performing an intraoral scan of the dental arches of the patient, these dental objects are scanned using an intraoral scanner. Typically, there are some regions of particular interest which need to be scanned in high detail, i.e. with a minimum or ideally no lack of scan data. An example of such a region can be a tooth, which needs some sort of restorative work, such as a repair or replacement. Therefore, it is important for the user to know that these areas are sufficiently covered by the obtained scan data, such that an accurate 3D representation can be built. If some parts of a tooth are not scanned, then there will be holes in the 3D representation. In some cases, the software is able to automatically fill in these holes representing missing data, but this will be an estimate. It is almost always preferred to cover all parts of the teeth/missing teeth with real scan data, since this allows for a more accurate 3D reconstruction. Another advantage is that the scan data related to the teeth can be stored in a patient management system.

In the scan workflow outlined above, the user typically looks at an external display while scanning the patient in order to follow the 3D reconstruction in real-time. This enables the user to know which parts have been sufficiently scanned and which parts need more scanning. In other words, the user utilizes the 3D representation on the display to estimate the scan coverage, i.e. which parts inside the oral cavity have been sufficiently scanned. A problem with this is that the 3D representation on the display will always be imaged from one angle; thus, there are many blind spots that the user cannot see, which may contain missing data. Therefore, the user needs to pause the scanning and rotate the 3D model to view it from different angles in order to ensure that all parts have been scanned sufficiently, i.e. ideally with no missing data/holes in the model.

The inventors have realized that instead of the user looking at the external display and rotating a 3D model to estimate the scan coverage, this metric can be reported in different ways that are more precise and allows the user to look into the mouth of the patient while scanning. The scan coverage may be divided into two related metrics: a global scan coverage and a local scan coverage. The former may be understood as a metric reporting how much of a given dental arch has been scanned. As previously mentioned, the dental arch typically features a number of dental objects such as teeth and possibly missing teeth, so the global scan coverage aims to assist the user in reporting whether these dental objects are sufficiently covered by scan data such that an accurate 3D representation can be generated. The local scan coverage may be understood as a metric reporting how much of a given dental object has been scanned. Thus, if a particular tooth is important to scan in high detail, the local scan coverage would preferably need to be very high for this tooth, whereas for other regions of lower importance, the local scan coverage can maybe be lower. Any of the local and global scan coverages may be determined as percentages; however, they may be reported to the user in a variety of ways, which is presented in further detail herein.

In some cases, it can be envisioned that the user marks some areas of interest on a visualization of the dental arch before initiating the scanning. This visualization may be presented on an external display or on a built-in display on the intraoral scanner. In this way, different thresholds for the local scan coverage may be defined by the scanner system. Once a given threshold is reached for the local scan coverage, then the system preferably informs the user via some feedback mechanism, such as light, color, or sound. This will allow the user to focus on scanning the patient, and then once a given tooth has been sufficiently scanned, the system informs the user, whereby the user can proceed to the next tooth, etc. In general, it is advantageous if the user is provided with the information of local scan coverage, i.e. how well a given dental object is scanned, without needing to look at an external display. It is further advantageous if the user is provided with the information of global scan coverage, i.e. how well the entirety of a given dental arch is covered by scan data. In particular, the inventors have realized that it is advantageous if the local/global scan coverage can be reported as a feedback provided by the intraoral scanner itself, such that the user can keep his eyes on the scanner and the patient's mouth while scanning.

The present disclosure therefore relates to a 3D scanner system for scanning a dental arch inside an oral cavity of a patient during a scanning session, the scanner system comprising: an intraoral scanner comprising an interaction device configured for initiating an action upon activation; and one or more processors configured to generate 3D scan data of at least a part of the dental arch. In preferred embodiments, the intraoral scanner further comprises some kind of feedback mechanism, such as a built-in display, an illumination ring, a light source, a plurality of light sources, or sound provided by a speaker. The embodiments presented below outline different ways of providing such a feedback mechanism. The detailed description will provide further details of these embodiments.

In one embodiment, the 3D scanner system comprises one or more processors configured to generate 3D scan data of at least a part of the dental arch and determine a local scan coverage measure based on whether a given dental object in the dental arch is sufficiently covered by the generated 3D scan data. In this embodiment, the scanner system further comprises an intraoral scanner comprising an interaction device configured for initiating an action upon activation; and a light source configured to change illumination, brightness and/or color, wherein the change is correlated with the local and/or global scan coverage measure.

In another embodiment, the 3D scanner system comprises an intraoral scanner comprising an interaction device configured for initiating an action upon activation, wherein the interaction device comprises one or more touch sensitive areas configured for detecting an input from a user based on capacitive sensing, wherein the scanner system further comprises one or more processors configured to generate 3D scan data of at least a part of the dental arch. In this embodiment, the intraoral scanner may further comprise an illumination ring, such as a light-emitting diode (LED) ring, which is located along the circumference of the touch sensitive ring. The illumination and/or color of the illumination ring may be correlated with the local/global scan coverage.

In another embodiment, the 3D scanner system comprises an intraoral scanner comprising an interaction device configured for initiating an action upon activation and a built-in display configured to display a visualization of the dental arch being scanned, wherein the scanner system further comprises one or more processors configured to generate 3D scan data of at least a part of the dental arch. In this embodiment, the visualization may be continuously generated and/or gradually expanded during the scanning session based on the scanned parts of the dental arch. The visualization of the dental arch in the built-in display on the intraoral scanner may be correlated with the local/global scan coverage.

In another embodiment, the 3D scanner system comprises an intraoral scanner comprising an interaction device configured for initiating an action upon activation; and an illumination unit which is integrated in the intraoral scanner, wherein the illumination unit is configured to provide illumination along at least a part of a circumferential or elliptical curve on a surface of the intraoral scanner, wherein the scanner system further comprises one or more processors configured to generate 3D scan data of at least a part of the dental arch. In this embodiment, a first part of the illumination unit may be configured for displaying information related to a lower arch of the patient, and a second part of the illumination unit may be configured for displaying information related to an upper arch of the patient. The illumination and/or color of the illumination unit may be correlated with the local/global scan coverage.

In another embodiment, the 3D scanner system comprises one or more processors configured to generate 3D scan data of at least a part of the dental arch. The system further comprises an intraoral scanner comprising an interaction device configured for initiating an action upon activation; and one or more illumination symbols, wherein the brightness and/or color of the illumination symbol(s) is correlated with the generation of 3D scan data, wherein the illumination symbol(s) are lit when 3D scan data is being generated during the scanning session. The illumination and/or color of the illumination symbol(s) may be correlated with the local/global scan coverage.

In another embodiment, the 3D scanner system comprises an intraoral scanner comprising a first and a second interaction device, each of said interaction devices configured for initiating an action upon activation, wherein the first and second interaction devices are located on opposite sides of the intraoral scanner; and a gyroscope configured to determine the orientation of the scanner, wherein the first and second interaction devices are interactively coupled to the gyroscope such that only one of said interaction devices is active at any given orientation of the scanner, and wherein the scanner system further comprises one or more processors configured to generate 3D scan data of at least a part of the dental arch.

In another embodiment, the 3D scanner system comprises a display for displaying a visualization of the dental arch; an intraoral scanner comprising an interaction device configured for initiating an action upon activation, wherein the interaction device comprises a button, such as a mechanical button or a touch sensitive button, arranged in a center surrounded by four other buttons, each of said four other buttons being configured to navigate among menu items in a graphical user interface provided by the display, wherein the button arranged in the center is configured to select a highlighted menu item upon being pressed, and wherein the scanner system further comprises one or more processors configured for continuously, during the scanning session, generating 3D scan data of at least a part of the dental arch.

In another embodiment, the 3D scanner system comprises an intraoral scanner comprising one or more reconfigurable buttons, wherein each reconfigurable button comprises a force sensor, such as a strain gauge sensor; and wherein the intraoral scanner further comprises a display configured for displaying one or more icons, texts, or animations, associated with the reconfigurable buttons, wherein the display covers the force sensors, and wherein the scanner system further comprises one or more processors configured to generate 3D scan data of at least a part of the dental arch.

The present disclosure further relates to an intraoral scanner comprising one or more reconfigurable buttons, wherein each reconfigurable button comprises a force sensor, such as a strain gauge sensor; and wherein the scanner further comprises a display configured for displaying one or more icons, texts, or animations, associated with the reconfigurable buttons, wherein the display covers the force sensors. The intraoral scanner may form part of the 3D scanner system disclosed herein.

DETAILED DESCRIPTION

Dental Object

Figure 1:
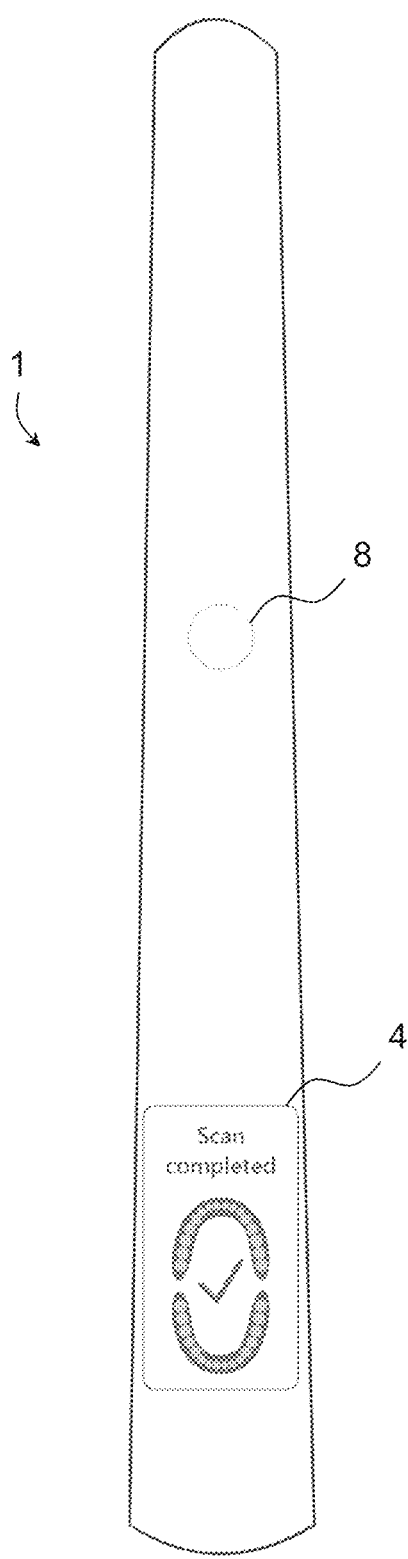
FIG. 1 shows an embodiment according to the present disclosure, wherein the intraoral scanner comprises a built-in display for displaying information related to the scanning session.

A dental object may be understood as a three-dimensional object inside the oral cavity of a person. Examples of dental objects include one or more of: tooth/teeth, implant(s), dental restoration(s), crowns, braces, dental prostheses, edentulous ridge(s), gingiva, and combinations thereof. The dental objects are typically situated in a dental arch in the patient's mouth. In some cases, the patient misses one or more teeth. In such cases, the scanner system is preferably configured to determine the scan coverage regardless. In some embodiments, a visualization of the scan coverage of the dental arch is generated and displayed, wherein the teeth and/or missing teeth are visualized e.g. using different colors.

Intraoral Scanner

The intraoral scanner may employ a scanning principle such as triangulation-based scanning, confocal scanning, focus scanning, ultrasound scanning, x-ray scanning, stereo vision, structure from motion, optical coherent tomography OCT, or another scanning principle. The intraoral scanner may be a handheld device.

In some embodiments, the intraoral scanner is operated by projecting a pattern and translating a focus plane along an optical axis of the intraoral scanner and capturing a plurality of 2D images at different focus plane positions. The series of captured 2D images corresponding to each focus plane then forms a stack of 2D images. The focus plane position is preferably shifted along the optical axis of the intraoral scanner, such that 2D images captured at a number of focus plane positions along the optical axis form said stack of 2D images for a given view of the object, i.e. for a given arrangement of the scanner relative to the object. After moving the intraoral scanner relative to the object or imaging the object at a different view, a new stack of 2D images for that view may be captured. The acquired 2D images may be processed to generate 3D scan data, also referred to herein as a sub-scan.

The focus plane position may be varied by means of at least one focus element, e.g., a moving focus lens. The intraoral scanner is generally moved and angled during a scanning session, such that at least some sets of sub-scans overlap at least partially, in order to enable stitching in a post-processing routine. The result of stitching is a digital 3D representation of the scanned object. Stitching, also known as registration, works by identifying overlapping regions of 3D surface in various sub-scans and transforming sub-scans to a common coordinate system such that the overlapping regions match, finally yielding the digital 3D model. An Iterative Closest Point (ICP) algorithm may be used for this purpose.

In other embodiments, the intraoral scanner is a triangulation-based scanner, which utilizes one or more cameras located at an angle relative to a projector unit to determine depth based on triangulation. In such embodiments, the intraoral scanner comprises one or more scan units, wherein each scan unit comprises a projector unit and one or more cameras. A scan unit may be understood herein as a unit comprising at least one projector unit and one or more cameras. In some embodiments, each scan unit comprises at least two cameras having at least partly overlapping fields of view along different camera optical axes. Preferably, each scan unit comprises at least four cameras having at least partly overlapping fields of view along different camera optical axes. A scan unit may further comprise one or more lenses such as collimation lenses or projection lenses. A camera may be understood herein as a device for capturing an image of an object. Each camera comprises an image sensor for generating an image based on incoming light e.g. received from the illuminated 3D object. Each camera may further comprise one or more lenses for focusing light.

As an example, the intraoral scanner may comprise one scan unit comprising one projector unit and at least two cameras. As another example, the intraoral scanner may comprise one scan unit comprising one projector unit and four cameras. In yet another example, the intraoral scanner may comprise at least two scan units, wherein each scan unit comprises a projector unit and two or more cameras. In yet another example, the intraoral scanner may comprise at least two scan units, wherein each scan unit comprises a projector unit and four cameras. In accordance with some embodiments, the projector optical axis and the camera optical axis of at least one camera define a camera-projector angle of approximately 5 to 15 degrees, preferably 5 to 10 degrees, even more preferably 8 to 10 degrees.

The scan units may further comprise a reflecting element. A reflecting element may be understood herein as an element configured to change the direction of light passing through or hitting the surface of said reflecting element. In particular, the reflecting element is preferably configured to change the direction of a center beam of the projected light from a projector unit from a direction substantially parallel to the longitudinal axis of the scanning device to a direction substantially orthogonal to said longitudinal axis. The reflecting element may be selected from the group of: mirrors, prisms, and/or combinations thereof. In preferred embodiments, the reflecting element is configured to reflect light from the projector unit(s) of at least one scan unit and/or reflect light from the surface of object being scanned and onto the image sensor(s) of at least one scan unit.

The intraoral scanner may utilize a time varying pattern featuring a sequence of different pattern configurations and/or colors, which is projected onto the dental object. In other embodiments, the intraoral scanner is configured to project a static pattern onto the surface of the dental object.

Projector Unit(s)

The intraoral scanner may comprise one or more projector units configured to generate an illumination pattern to be projected on a three-dimensional dental object during a scanning session. The projector unit(s) preferably comprises a light source, a mask having a spatial pattern, and one or more lenses such as collimation lenses or projection lenses.

The light source may be configured to generate light of a single wavelength or a combination of wavelengths (mono- or polychromatic). The combination of wavelengths may be produced by using a light source configured to produce light (such as white light) comprising different wavelengths. Alternatively, the projector unit(s) may comprise multiple light sources such as LEDs individually producing light of different wavelengths (such as red, green, and blue) that may be combined to form light comprising the different wavelengths. Thus, the light produced by the light source may be defined by a wavelength defining a specific color, or a range of different wavelengths defining a combination of colors such as white light.

In some embodiments, the intraoral scanner comprises a light source configured for exciting fluorescent material to obtain fluorescence data from the dental object such as from teeth. Such a light source may be configured to produce a narrow range of wavelengths. The intraoral scanner may additionally or alternatively comprise an infrared light source configured to generate wavelengths in the infrared range, such as between 700 nm and 1.5 μm. In some embodiments, the intraoral scanner comprises a light source selected from the group of: Infrared (IR) light source, near-infrared (NIR) light source, blue light source, violet light source, and/or combinations thereof.

The projector unit(s) may be Digital Light Processing (DLP) projectors using a micro mirror array for generating a time varying pattern, or a diffractive optical element (DOF), or front-lit reflective mask projectors, or micro-LED projectors, or Liquid crystal on silicon (LCoS) projectors or back-lit mask projectors, wherein a light source is placed behind a mask having a spatial pattern, whereby the light projected on the surface of the dental object is patterned. The pattern may be dynamic, i.e. such that the pattern changes over time, or the pattern may be static in time, i.e. such that the pattern remains the same over time. The projector unit(s) may comprise a collimation lens for collimating the light from the light source, said collimation lens being placed between the light source and the mask. The projector unit(s) may further comprise one or more focus lenses configured for focusing the light at a predefined focus distance.

The intraoral scanner preferably further comprises optical components for directing the light from the light source to the surface of the dental object. The specific arrangement of the optical components depends on whether the intraoral scanner is a focus scanning apparatus, a triangulation-based scanner, or any other type of scanning device. A focus scanning apparatus is further described in U.S. Pat. No. 8,878,905 B2 filed on 17 Jun. 2010 by 3Shape A/S, which is incorporated herein in its entirety. A triangulation-based scanner is disclosed in WO 2023/117981 A1 filed on 19 Dec. 2022 and in WO 2023/187181 A1 filed on 31 Mar. 2023, which are incorporated herein by reference in their entirety.

The light reflected from the dental object in response to the illumination of the dental object is directed, using optical components of the intraoral scanner, towards the image sensor(s). The image sensor(s) are configured to acquire one or more images based on the incoming light received from the illuminated dental object. The image sensor may be a high-speed image sensor such as an image sensor configured for acquiring images with exposures of less than $\frac{1}{1000}$ second or frame rates in excess of 250 frames pr. second (fps). As an example, the image sensor may be a rolling shutter (CCD) or global shutter sensor (CMOS). The image sensor(s) may be a monochrome sensor including a color filter array such as a Bayer filter and/or additional filters that may be configured to substantially remove one or more color components from the reflected light and retain only the other non-removed components prior to conversion of the reflected light into an electrical signal. For example, such additional filters may be used to remove a certain part of a white light spectrum, such as a blue component, and retain only red and green components from a signal generated in response to exciting fluorescent material of the teeth. The image sensor may also be a color image sensor for generating color images.

Processors

The 3D scanner system preferably further comprises one or more processors configured to generate scan data by processing two-dimensional (2D) images acquired by the intraoral scanner. The processor(s) may be part of the intraoral scanner, or they may be external to the scanner such as part of a computer system. As an example, the processor(s) may be selected from the group of: central processing units (CPU), accelerators (offload engines), general-purpose microprocessors, graphics processing units (GPU), neural processing units (NPU), application-specific integrated circuits (ASIC), field-programmable gate arrays (FPGA), dedicated logic circuitry, dedicated artificial intelligence processor units, or combinations thereof. In some embodiments, the intraoral scanner comprises a Field-programmable gate array (FPGA) and an ARM processor.

The scan data comprises information relating to the three-dimensional dental object. The scan data may comprise any of: 2D images, 3D point clouds, depth data, texture data, intensity data, color data, and/or combinations thereof. As an example, the scan data may comprise one or more point clouds, wherein each point cloud comprises a set of 3D points describing the three-dimensional dental object. As another example, the scan data may comprise images, wherein each image comprises image data. In some cases, the image data contains image coordinates and a timestamp $(x, y, t)$, wherein depth information can be inferred from the timestamp. The image sensor(s) of the intraoral scanner may acquire a plurality of 2D images of the dental object in response to illuminating said object using the one or more projector units. The plurality of 2D images may also be referred to herein as a stack of 2D images.

The 2D images may subsequently be provided as input to the one or more processors, which are configured to process the 2D images to generate scan data, such as depth map(s). The processing of the 2D images may comprise the step of determining which part of each of the 2D images are in focus in order to deduce/generate depth information from the images. The depth information may be used to generate 3D point clouds comprising a set of 3D points in space, e.g., described by cartesian coordinates $(x, y, z)$. Each 2D/3D point may furthermore comprise a timestamp that indicates when the 2D/3D point was recorded, i.e., from which image in the stack of 2D images the point originates. The timestamp is correlated with the z-coordinate of the 3D points, i.e., the z-coordinate may be inferred from the timestamp. Accordingly, one output of the processor may be scan data, and the scan data may comprise image data and/or depth data, e.g. described by image coordinates and a timestamp $(x, y, t)$ or alternatively described as $(x, y, z)$. The intraoral scanner may be configured to transmit other types of data in addition to the scan data. Examples of types of data include 3D information, texture information, infra-red (IR) images, fluorescence images, reflectance color images, x-ray images, and/or combinations thereof.

Wireless Module

The intraoral scanner preferably comprises a module for transmitting data, such as images or point clouds, to one or more external devices, such as a computer system. The module may be a wireless module configured to wirelessly transfer data from the intraoral scanner to the computer system. The wireless module may be configured to perform various functions required for the intraoral scanner to wirelessly communicate with a computer network. The wireless module may utilize one or more of the IEEE 802.11 Wi-Fi protocols/integrated TCP/IP protocol stack that allows the intraoral scanner to access the computer network. The wireless module may include a system-on-chip having different types of inbuilt network connectivity technologies. These may include commonly used wireless protocols such as Bluetooth, ZigBee, Wi-Fi, WiGig (60 GHz Wi-Fi) etc. The intraoral scanner may further (or alternatively) be configured to transmit data using a wired connection, such as an ethernet cable.

In some embodiments, the intraoral scanner is configured to acquire sets of images, wherein a set of images comprises an image from each camera of the intraoral scanner. As an example, if the intraoral scanner comprises four cameras, the intraoral scanner may continuously acquire sets of four images, wherein the correspondence problem is solved continuously within each set of images. The intraoral scanner may be configured to solve the correspondence problem in two main steps: a first step, wherein image features in the images within a set of images are determined, and a second step, wherein 3D points are determined based on triangulation. Finally, a 3D representation of the scanned object may be generated based on the 3D points. In some embodiments, the intraoral scanner comprises a first processor, wherein the first processor is configured to execute the step of determining the image features in the images. The intraoral scanner may employ hardware acceleration, e.g. by including a neural processing unit as the first processor.

In some embodiments, the intraoral scanner is configured to transmit sub-scans (e.g. depth maps) and/or the acquired images, wherein said images have been compressed using a suitable compression. The data, such as the images or the sub-scans may be transmitted wirelessly. As an example, a lossy compression may be utilized, such as a JPEG compression. An advantage of using a lossy compression is that the data transfer rate (i.e. the bit rate) is lowered, whereby the transfer rate is enhanced for wireless transmission. Consequently, a more smooth scanning experience is created, wherein the user experiences very low latency between acquisition of data and generation of the 3D representation. Another advantage of utilizing compression of the data is that it lowers the bandwidth requirement of a wireless connection (e.g. Wi-Fi) between the intraoral scanner and an external device. In some embodiments, the intraoral scanner is configured to continuously transmit compressed images to an external device using a video compression standard, such as H.264 or H.265. Accordingly, the intraoral scanner may be configured to stream a video of images to an external device, such as a computer system, which is configured to decode and/or display the images. The 3D scanner system may comprise a display for displaying the video stream.

Interaction Device

In some embodiments, the intraoral scanner comprises one or more interaction devices configured for initiating an action or operation upon activation. The interaction device (s) may be selected from the group of: mechanical buttons, reconfigurable buttons, touch sensitive areas or buttons, touchscreens, and/or combinations thereof. The interaction device(s) may be recessed in a surface of the intraoral scanner. The interaction device(s) may be configured to initiate one or more actions, such as: initiating a scan, stopping a scan, navigating in a graphical user interface, selecting a menu item, acquiring a single image, proceeding to a next or previous step in a scanning workflow, undoing a previous action, initiating a fluorescence or infrared scan, interacting with the 3D representation (e.g. zoom and/or rotate), uploading the 3D representation to the cloud, etc. In some embodiments, the interaction device comprises one or more mechanical buttons and/or one or more reconfigurable buttons.

Scan Coverage

In some embodiments, one or more processors of the scanner system are configured for determining a local and/or global scan coverage measure. These measures may be based on whether the dental object(s) in the dental arch are sufficiently covered by the generated scan data. Global scan coverage may be understood as how much of the dental arch(es) inside the oral cavity has been scanned using the intraoral scanner. In other words, how much of the dental arch(es) are covered by scan data, e.g. 3D scan data. One example of how to estimate the global scan coverage is to compare the current scan data to a previously obtained 3D representation of the same patient or of a generic patient. The comparison can be based on a variety of parameters. For instance, the previously obtained 3D representation may have a given total surface area. Then, as the patient is scanned and a new 3D representation is continuously built, a surface area of the new 3D representation may be determined and compared to the surface area of the previously obtained 3D representation. Then, the global scan coverage may be determined as the ratio of the two surface areas.

The global scan coverage may also be determined using other parameters, such as the amount of 3D scan data generated and/or the density of the 3D scan data. As an example, a typical 3D representation of a full dental arch may contain a given approximate number of sub-scans, i.e. depth maps, that are stitched together. Then, the generated 3D scan data may be compared to the typical number of total sub-scans, whereby a ratio can be determined to estimate a global scan coverage. Another way of estimating the global scan coverage is if the user enters the number of teeth that the patient has in the dental arch to be scanned. Then, while scanning the teeth, the processor(s) may be configured to automatically determine the individual teeth, such that the number of scanned teeth can be determined. The number of scanned teeth can then be compared to the number of teeth entered before the scan to determine a ratio, e.g. 12 out of 16 teeth scanned. The same principle may apply to other dental objects than teeth, e.g. missing teeth, and dental restorations such as crowns. In other embodiments, details of the patient's dentition, such as the patient's teeth, missing teeth, dental restorations, etc. may be stored and accessed in a patient management system. Thus, the scanner system may utilize said information from the patient management system to determine a global scan coverage during scanning.

Furthermore, the one or more processors may be configured for determining a local scan coverage measure. The local scan coverage measure may be based on whether a given dental object in the dental arch is sufficiently covered by the generated 3D scan data. In other words, the local scan coverage may be considered a metric to gauge how well a given dental object is covered by the generated scan data. As an example, if a tooth is only imaged from one side, then there would not exist any data for digitally reconstructing the other side of the tooth; in that case, the local scan coverage associated with that tooth would be poor. For regions of interest, e.g. teeth that need replacement or for tooth preparations, it is generally important to generate 3D scan data for ideally the entire area, such that no missing data exist in the region of interest. Therefore, it is of great interest to the user to know what the scan data coverage of a given dental object is, which may then be captured by the local scan coverage measure. In some embodiments, the local scan coverage is based on the density of the generated 3D scan data, wherein the density is measured in number of data points per area or volume. As an example, the 3D scan data may be point clouds, and the local scan coverage may be based on the density of said point clouds. Alternatively or in addition hereto, the local scan coverage measure may be based on the amount of 3D scan data generated for a given dental object in the dental arch.

In some embodiments, a tooth segmentation algorithm is executed, wherein said algorithm is configured to classify the scanned parts of the dental arch into tooth tissue and non-tooth tissue. Preferably, the algorithm is further configured to uniquely identify the teeth, e.g. in accordance with a dental notation system. Thus, the 3D scanner system may be configured to automatically identify teeth in the dental arch. The tooth segmentation algorithm may be executed continuously and in real-time, or alternatively the algorithm may be executed when the user pauses or stops the scanning. The scanner system may then be able to determine the type of teeth and the number of teeth. This information may be utilized to determine the local and/or the global scan coverage. A suitable tooth segmentation algorithm is fully described in PCT application PCT/EP2023/069452 filed on 13 Jul. 2023 by 3Shape A/S, which is hereby incorporated herein by reference in its entirety.

The present inventors have realized a variety of different ways to report any of the local and/or the global scan coverage measures. As a few examples, these metrics may be reported or displayed in a built-in display on the intraoral scanner, or they may be reported using differently colored light e.g. in the display or provided by one or more feedback light sources located on the scanner. In some embodiments, the local/global scan coverage is reported as a number, such as a ratio or a percentage; in other embodiments, the intraoral scanner provides one or more feedbacks once a given threshold value of the local/global scan coverage is reached. In some embodiments, the local scan coverage is reported/visualized using a color gradient in a visualization of the dental arch being scanned. As an example, the color gradient may be a linear color gradient between two separate colors, such as green and yellow. The local scan coverage may be visualized in an integrated display on the scanner.

In some embodiments, the scanner system is configured to automatically segment/classify the 3D representation into gingiva and teeth, e.g. using one or more computer-implemented algorithms. As an example, the algorithms may be based on one or more neural networks trained to perform said classification of tissue into gingiva and teeth. In some embodiments, the scanner system is configured to automatically determine the boundary between gingiva and teeth, e.g. based on the output from the aforementioned algorithm(s).

Scanner with Display

In some embodiments, the intraoral scanner comprises a display. A display may be understood herein as an electronic display or display device for presentation of images, text, or video. The display may be selected from the group of: flat panel displays, light-emitting diode (LED) displays, organic LED (OLED) displays, liquid-crystal display (LCD) displays, electronic ink (E Ink) displays, or other suitable displays. As an example, the display may be a flat panel display comprising an array of light-emitting diodes as pixels. As another example, the display may be an electrophoretic display, also referred to as an e-ink display or an electronic paper display. An electrophoretic display is typically configured to mimic the appearance of ordinary ink on paper and reflect ambient light like paper. An advantage of many e-ink displays over conventional flat panel displays is the ability to hold static text and images indefinitely without electricity. Other advantages include a wider viewing angle than most light-emitting displays and that e-ink display are typically more comfortable to read.

The display is preferably a built-in display, i.e. such that it is integrated in the intraoral scanner. The display may be integrated in a surface of the scanner, e.g. such that it is flush with the surface. The display may be configured to display information related to the scanning session. As an example the intraoral scanner may be configured to display the status of the scanner in the display, wherein the status is selected from the group of: connecting, ready to scan, ready to scan lower arch, ready to scan upper arch, ready to scan left bite, ready to scan right bite, scanning, patient identified, scanning complete, scan uploaded, and/or combinations thereof.

Figure 4:
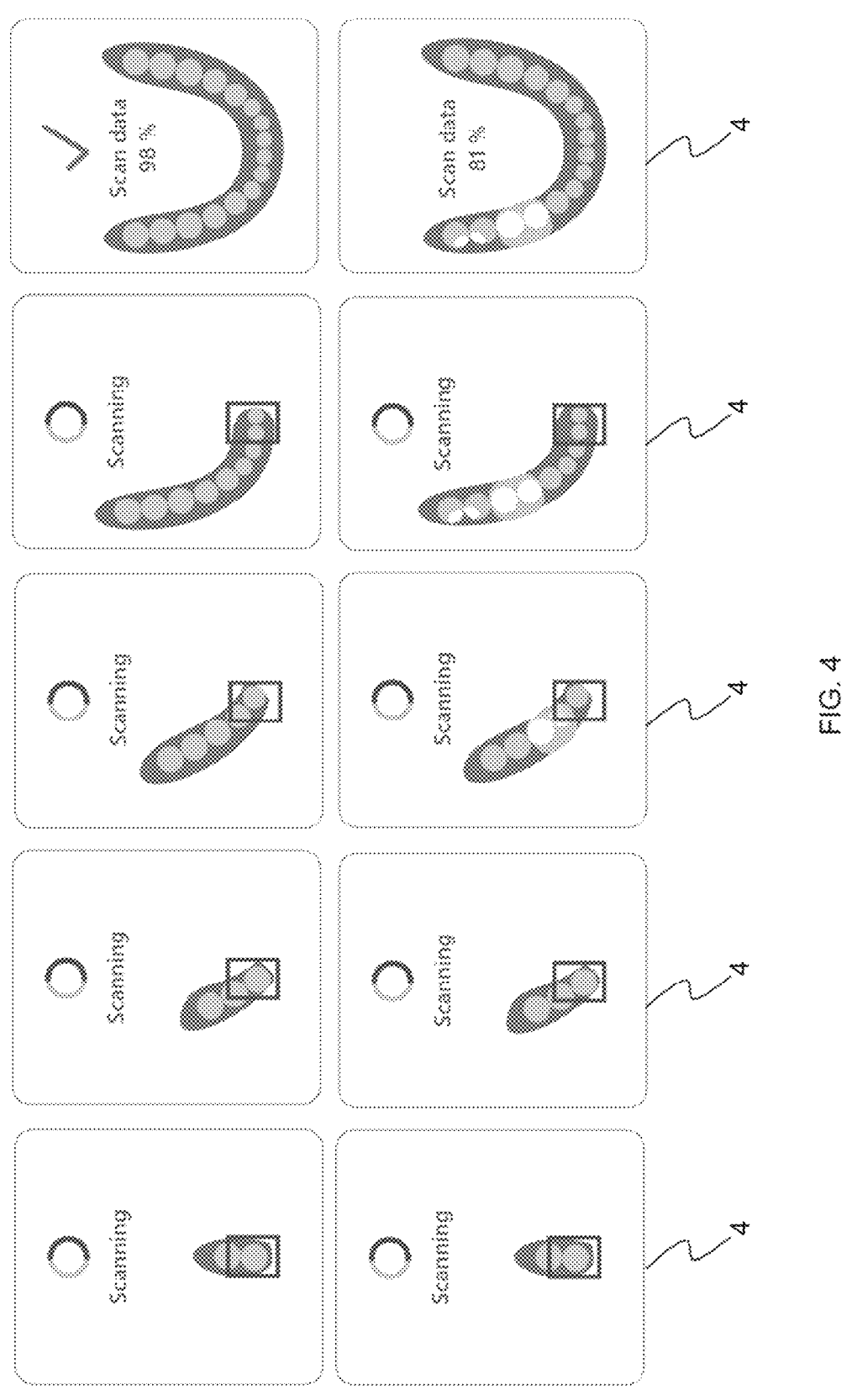
FIG. 4 shows another example of how a built-in display can be utilized; in this example, the visualization of the dental arch (incl. teeth) is gradually built along with the scanning. Different colors may be utilized to report local scan coverage.
Figure 5:
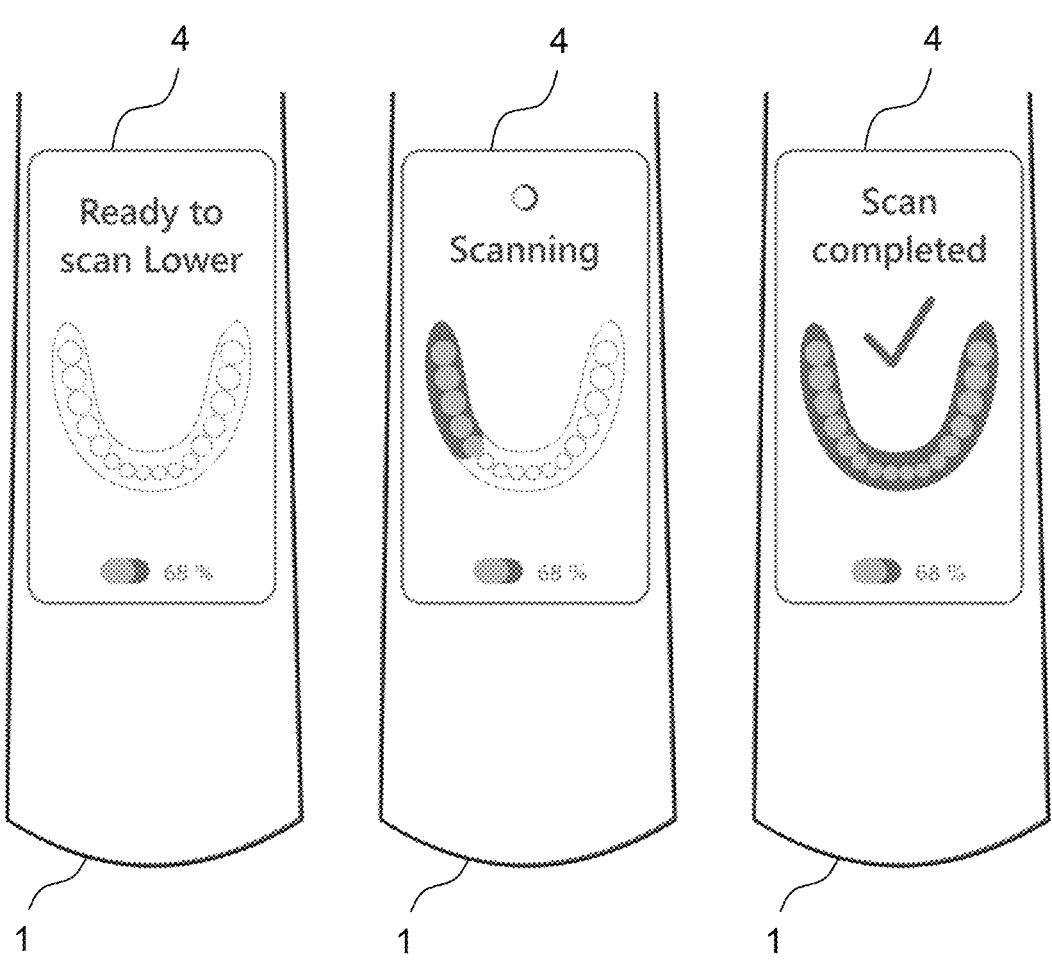
FIG. 5 shows another example of how a built-in display can be utilized; in this example, the visualization of the dental arch (incl. teeth) is outlined before scanning is initiated. Then, the outline may be filled in gradually, e.g. using one or more colors, during the scanning.

The display may be further configured to display a visualization of the dental arch being scanned. An example of an intraoral scanner with a built-in display is shown in FIGS. 1-5. The visualization of the dental arch does not imply that a 3D rendering of the arch is shown in the display. On the contrary, it may be that the visualization is a more simple 2D visualization, which serves the purpose of schematically showing the dental arch or showing a generic 2D illustration of a dental arch. In some embodiments, the 3D scanner system comprises a display, which is external to the scanner, wherein said display is configured to display any of the visualizations e.g. of the dental arch, which is disclosed herein. In the example of FIG. 4, the dental arch is visualized gradually as scan data is captured/generated, such that the visualization is continuously generated during the scanning session. In the example of FIG. 5, an outline of the dental arch is visualized before the dental arch has been scanned. In some embodiments, each dental object in the dental arch, e.g. each tooth or missing tooth, may be symbolically visualized in the display, e.g. by dots or circles. The dots or circles may be given a color, which is correlated with the local scan coverage. As an example, initially all of the dental objects in the dental arch may be colored grey or white. Then, once the dental objects have been scanned, a given tooth symbol may turn into a first color, e.g. green, if sufficient 3D scan data of that particular tooth has been generated; conversely, the tooth symbol may turn into a second color, e.g. yellow, e.g. if some part(s) of the tooth has not been scanned or if the scan data is insufficient, which will result in holes in the generated 3D representation. The color change of the visualization/tooth symbols may occur continuously during the scanning session. Alternatively, the color change of the visualization may occur when the user pauses or stops the scanning.

In a typical scan workflow, each dental arch is scanned individually. Thus, the dental arches may be visualized in the built-in display one at a time. Alternatively, they may be visualized together e.g. when the scan is completed. An advantage of the built-in display is that the user is aware of the progress of the scanning while looking inside the patient's mouth instead of at an external screen. Preferably, the visualization changes dynamically and continuously as images are acquired and scan data is generated. Accordingly, the visualization of the dental arch may change continuously and in real-time and be synchronized with the generation of the 3D representation of the patient's teeth. This has the benefits that it provides a dynamic feedback to the user and that the user can see both the progress but also the scan coverage directly on the display on the intraoral scanner. In other embodiments, the visualization changes upon pausing the scanning, such that the user can inspect the progress of the scan in the visualization in the display.

In some embodiments, the visualization of the dental arch is continuously generated and/or gradually expanded during the scanning session based on the scanned parts of the dental arch. An example of this is shown in FIG. 4. Initially, the processor(s) may not be able to determine where in the mouth the user has initiated the scan. Therefore, the visualization may be built gradually as more scan data is generated, rather than displaying a predetermined map or outline of the dental arch. As an example, the user may start scanning on one tooth, which is then visualized in the display. As mentioned above, the color of the visualized tooth may change once enough 3D scan data has been generated for that tooth. In this case, the color change is then used as a cue to the user that he/she may proceed with scanning another tooth or area. As the scanning proceeds and more areas are imaged, the visualization is expanded according to the new areas. The field of view of the scanner may be visualized in the display, e.g. using a rectangle or another suitable shape. FIG. 4 shows how the visualization may expand as more data is captured. In the top row, all of the areas are scanned with sufficient density, e.g. with enough scan data for each area, whereby the dots or circles are colored using a similar color, such as green. In the bottom row, there are some areas, e.g. a couple of teeth, for which there is a lack of scan data. In other words, the digital 3D representation will contain holes or missing data in these areas of insufficient scan coverage. These areas are preferably highlighted in the visualization, e.g. using a separate color, such as yellow. Thereby, the user is informed and is able to revisit those areas using the scanner. Thus, FIG. 4 provides one example of how the visualization of the dental arch can be correlated to the local and/or global scan coverage. Another example is provided in FIG. 5, in which a schematic outline of the dental arch and teeth is shown. This may then be filled in during scanning as scan data is generated for the various parts of the dental arch.

Figure 13:
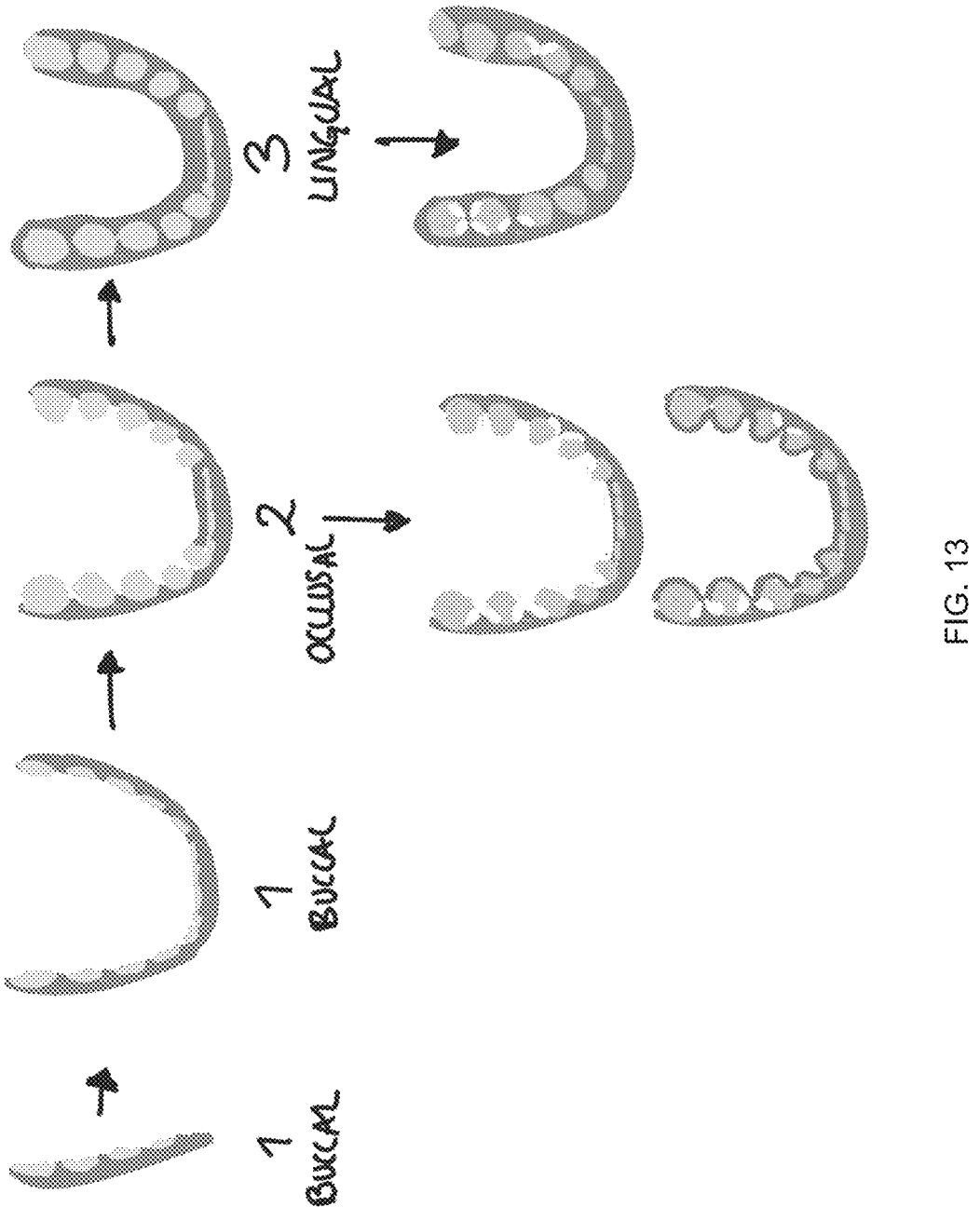
FIG. 13 shows an example of how the dental arch may be visualized in the built-in display.

In some embodiments, areas of low scan data density, e.g. defined by a predefined threshold value, are colored in the visualization of the dental arch using a color gradient correlated with the local scan coverage. In some embodiments, a tooth classification algorithm is executed to automatically classify the 3D representation into gingiva and teeth. The algorithm may run continuously and in real-time. In some embodiments, the local scan coverage is based on scan data density, e.g. the density of point clouds used to stitch the 3D representation. The visualization in the display may be colored according to the density of the generated scan data, e.g. the number of data points per volume. In general, the 3D representation will always have a boundary. Beyond this boundary, the density of scan data will be zero. Therefore, in some cases the boundary is colored according to the color gradient, e.g. yellow; in other cases, the boundary is ignored/exempted from the given color scheme. It may also be that any boundary on tooth surface is always highlighted, e.g. using yellow, in the visualization, such that the user is informed that here exists an incomplete tooth in the 3D representation. This may be based on the local scan coverage combined with the aforementioned tooth/gingiva classification. In some embodiments, the 3D scanner system is configured to distinguish between a boundary e.g. on a teeth surface or on the gingiva and holes in the 3D representation. Thus, the scanner system may be configured to determine one or more boundaries and/or hole(s) in the 3D representation. It may be further configured to highlight said boundaries and/or hole(s) e.g. using separate colors. This is illustrated in FIG. 13, which shows that separate colors, such as yellow and grey, may be utilized to highlight boundaries and/or hole(s).

In some embodiments, the visualization of the dental arch is a fixed 2D projection, e.g. viewed such that the occlusal surface is visible. The visualization may be a schematic visualization, e.g. shown for the purpose of displaying the progress of the scan and/or the quality/coverage of the generated scan data. Alternatively, the visualization may be a 2D projection of the generated 3D representation of the scanned dental arch. In some embodiments, the 2D projection is expanded such that surfaces normally obscured from the viewpoint are shown in the projection, e.g. vertical surfaces of the teeth are shown in the projected/expanded view. In that way, boundaries, such as any boundary on the teeth or the interface between the teeth/gingiva will become more clearly visible in the visualization. The expanded 2D projection may be colored according to the color scheme mentioned previously, e.g. based on the local scan coverage.

Touch Sensitive Areas

Figure 6:
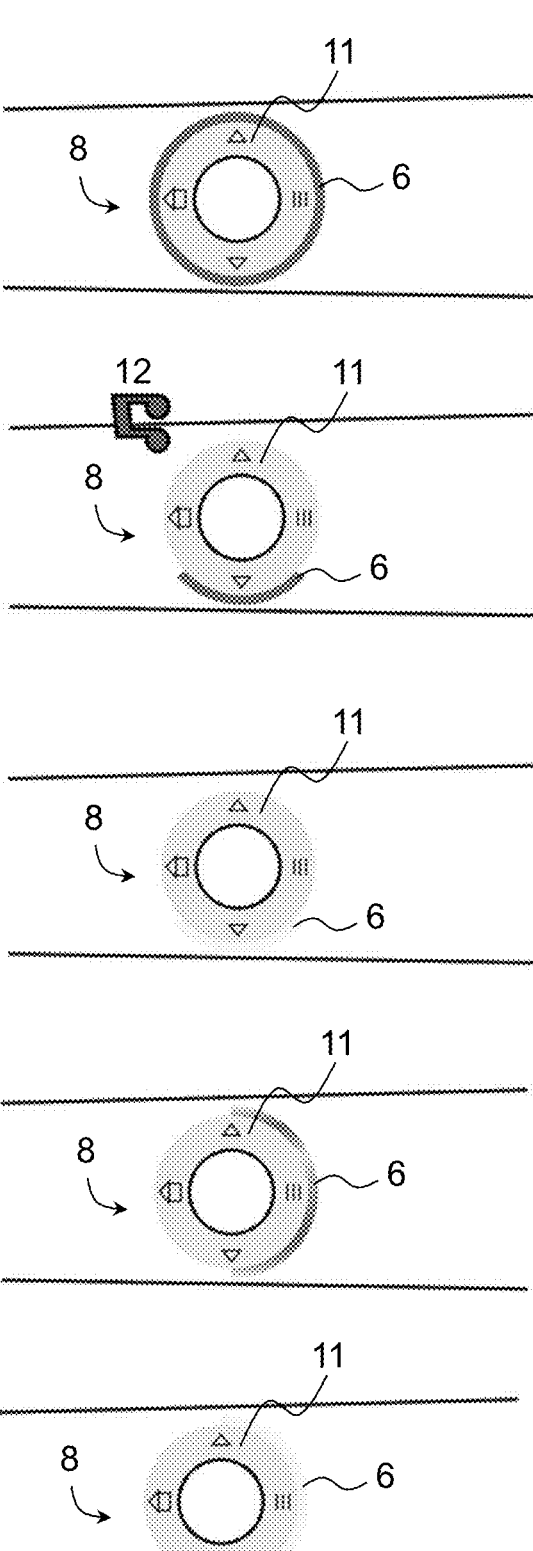
FIG. 6 shows an embodiment of an intraoral scanner, wherein the scanner comprises a touch sensitive ring configured for detecting an input from a user. In this example, the scanner further comprises an illumination ring located along the circumference of the touch sensitive ring.

The intraoral scanner may comprise one or more interaction devices configured for initiating an action or operation upon activation. The interaction device(s) may comprise one or more touch sensitive areas configured for detecting an input, such as one or more gestures, from a user based on capacitive sensing or force touch sensing. As an example, the touch sensitive areas may constitute a touch sensitive ring, which is configured to detect a user's input using capacitive or force touch sensing. The interaction device may utilize a combination of touch technology and traditional buttons, i.e. mechanical buttons, or strain gauges. As an example, the interaction device may comprise four mechanical buttons that lie beneath the touch sensitive areas, such that the interaction device is able to register multiple commands. Thus, in some embodiments, the interaction device further comprises at least four mechanical buttons located beneath the touch sensitive area(s). Such an embodiment is illustrated in FIG. 6. A first mechanical button may be configured to, upon activation, proceed to a next step in the scanning session, and a second mechanical button may be configured to, upon activation, proceed to a previous step in the scanning session. This has the advantage that the user can easily go back and forth in the scanning workflow (e.g. scanning the upper/lower dental arch or the patient's bite) directly by pressing a button on the intraoral scanner.

In some embodiments, the touch sensitive ring is based on force touch technology rather than capacitive sensing. This may be achieved by placing one or more strain gauges under the touch sensitive ring, wherein each of said strain gauges are configured to detect strain/deformation in the material(s) above the strain gauge. As an example, four strain gauges may be positioned, e.g. in a cross, under the circular ring. The cross may be oriented such that each icon, e.g. shown in FIG. 6, is associated with a strain gauge placed underneath. Then, the four strain gauges are configured to detect user input such as touch presses and/or swiping actions. Thus, the strain gauges may be configured to emulate capacitive sensing, however with some advantages over capacitive sensing. An advantage of utilizing force touch technology based on strain gauges is that the touch sensitive ring may be operated in wet conditions and when using gloves. This can be challenging when operating touch sensitive areas based on capacitive sensing. The scanner may further be configured to provide haptic feedback correlated with use of the touch sensitive ring. As an example, the scanner may provide haptic feedback, e.g. vibration, when the user presses an icon on the touch sensitive ring and/or when the user performs a swiping action using the touch sensitive ring.

In some embodiments, the intraoral scanner further comprises an illumination ring, such as a light-emitting diode (LED) ring, which may be located along the circumference of the touch sensitive areas. The illumination ring preferably constitutes a full circle but in some cases it may only form part of a circle. Other shapes can also be envisioned. The illumination ring may be configured to display a simplified visualization of the dental arch being scanned. The visualization may simply be the illumination of the ring itself, e.g. wherein a first part of the illumination ring is configured for displaying information related to a lower arch of the patient, and wherein a second part of the illumination ring is configured for displaying information related to an upper arch of the patient. The first and second parts may each constitute a half circle such that the first and second parts in combination constitutes a full circle. A third and/or fourth part of the illumination ring may be configured for displaying information related to a bite scan procedure within the scanning session. The third and fourth parts may be opposite to each other and the third or fourth part is preferably used to display information related to a left or right bite scan procedure. Furthermore, the third and/or fourth parts may overlap the first and/or second part of the illumination ring.

The illumination, brightness, and/or color of the illumination ring may be correlated with the generated scan data of a given dental arch, such that the illumination ring is configured to inform the user of the local/global scan coverage. Thus, the illumination ring may be configured to visualize a progress of the scanning session and/or whether sufficient scan data has been obtained. The illumination ring may be configured to visualize the part(s) of the upper/lower arch which has been scanned, i.e. for which 3D scan data has been acquired. The illumination ring may be configured to utilize one or more colors to visualize the local/global scan coverage.

As an example, green may be used to denote areas for which sufficient 3D scan data has been generated, and yellow may be used to denote areas for which insufficient 3D scan data exists, i.e. areas which have a low local scan coverage. Other colors may also be utilized. Alternatively, the brightness of the illumination ring may be correlated with the local and/or global scan coverage. Once a given part of the illumination ring, e.g. the first part, is fully green (or another suitable color), the scanner may be configured to provide a sound for signaling that the user can move on to scanning the other dental arch (e.g. upper or lower jaw). This may similarly be implemented for the third and/or fourth part, i.e. when the bite scan is completed the scanner may provide a sound. This is exemplified in FIG. 6. Finally, the illumination ring may be configured to be fully lit with a predefined color, such as green, once the scanning session is completed.

Feedback Light Source

In some embodiments, the intraoral scanner comprises a feedback light source, such as a light-emitting diode (LED), located on the intraoral scanner. The feedback light source is preferably located such that it is visible from outside the scanner. The feedback light source is preferably configured to change illumination, brightness and/or color, wherein the change is correlated with the local and/or global scan coverage measure. In preferred embodiments, the feedback light source is configured to light up and/or change color when the local scan coverage measure reaches a predefined threshold value, such that the intraoral scanner signals when enough 3D scan data has been obtained for a given dental object. It may similarly be configured to be associated with the global scan coverage. As an example, the feedback light source may turn green once enough 3D scan data has been generated for a given dental object, such as a tooth. Thereby, the user receives a feedback, which is visible inside the patient's mouth while scanning, whereby the user knows to proceed to scanning the next dental object in the mouth. The feedback light source may further be used for displaying a status of the scanner. In some embodiments, the feedback light source is configured to change color based on detecting the presence of bacteria, e.g. in response to a fluorescence emission captured by the scanner.

Illumination Unit

Figure 7:
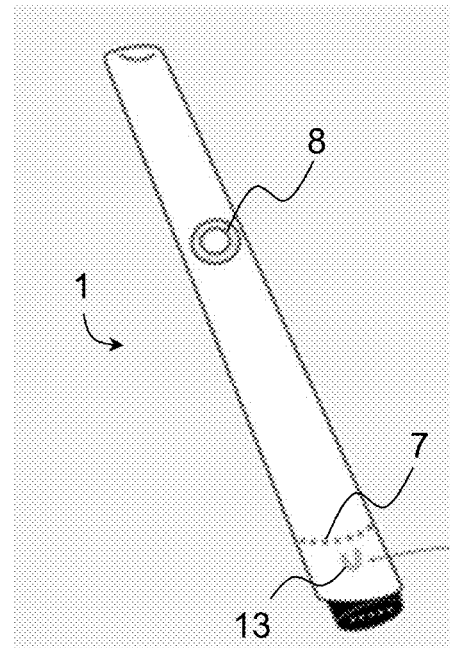
FIG. 7 shows an embodiment of an intraoral scanner, wherein the scanner comprises an integrated illumination unit configured to provide illumination along at least a part of a circumferential or elliptical curve on a surface of the intraoral scanner.

In some embodiments, the intraoral scanner comprises an illumination unit. The illumination unit is preferably integrated in the intraoral scanner, such as in a surface of the scanner, such that light emitted from the illumination unit is visible from outside of the scanner. In that way the illumination unit can provide light intended as feedback to the user. The illumination unit may be configured to provide illumination along at least a part of a circumferential or elliptical curve on a surface of the intraoral scanner. However, other curves may also be envisioned without departing from the scope of the disclosure. In some embodiments, the circumferential or elliptical curve forms a closed loop around the intraoral scanner. The illumination unit may comprise a plurality of light sources, such as a plurality of individual LEDs. The plurality of light sources may be arranged along the aforementioned circumferential or elliptical curve around the scanner, such as in a closed loop around the scanner. Such an embodiment is illustrated in FIG. 7. As an example, the light sources may correspond to predefined parts of the dental arches, or each light source may correspond to a dental object in the upper and/or lower arch.

In preferred embodiments, a first part of the illumination unit is configured for displaying information related to a lower arch of the patient, and a second part of the illumination unit is configured for displaying information related to an upper arch of the patient. As an example, a first subset of light sources may constitute the first part of the illumination unit, and a second subset of light sources may constitute the second part of the illumination unit. In this example, the first part of the illumination unit may be configured to be lit when scanning the lower arch, and the second part of the illumination unit may be configured to be lit when scanning the upper arch. In embodiments, wherein the illumination unit comprises a plurality of light sources arranged along a closed loop around the intraoral scanner, the first part preferably covers approximately half of the closed loop, and the second part preferably covers approximately the other half of the closed loop. The brightness and/or color of the light sources/illumination unit is preferably correlated with the generated 3D scan data, such that the illumination unit is configured to visualize the scan coverage, i.e. which parts of the dental arch(es) have been scanned. At least one purpose hereof is to aid the user when scanning the jaws of the patient, in particular when scanning the upper jaw of the patient.

The illumination unit may be configured such that a first color of the light sources/illumination unit indicates that the generated 3D scan data is sufficient, and further configured such that a second color of the light sources indicates that the generated 3D scan data is insufficient. A sufficient amount of generated scan data for a given dental object may be understood as that dental object having a local scan coverage above a certain predefined threshold value. In other words, it may imply that the dental object has been imaged from a variety of angles/viewpoints in order to generate/reconstruct a smooth digital surface of the dental object with a minimum of missing data/holes in the reconstructed model.

Illumination Symbols

In some embodiments, the intraoral scanner may further comprise one or more illumination symbols. The brightness and/or color of the illumination symbol(s) may be correlated with the generation of 3D scan data and/or correlated with the local/global scan coverage. As an example, the illumination symbol(s) may be lit when 3D scan data is being generated during the scanning session. As another example, the illumination symbol(s) may be lit with a first color when the scanner is ready to scan and lit with a second color when 3D scan data is being generated. In preferred embodiments, the intraoral scanner comprises two illumination symbols located on opposite sides of the scanner, wherein a first illumination symbol is lit when scanning a first dental arch, and wherein a second illumination symbol is lit when scanning a second dental arch. The first and second dental arches may be the lower and upper arch/jaw, respectively.

Gyro-Activated Buttons

In some embodiments, the intraoral scanner comprises a first interaction device and a second interaction device. The first and second interaction devices may be mechanical buttons, such as buttons recessed in a surface of the scanner. Alternatively, the first and second interaction devices may be based on touch sensitive technology or force touch technology. The first and second interaction devices may be located on opposite sides of the intraoral scanner. They may be configured for the same purpose, e.g. for starting/stopping the scanner or for another purpose. Furthermore, the two buttons/interaction devices may in preferred embodiments only be active one at a time. One way to achieve this is by coupling the two interaction devices to a gyroscope in the scanner, wherein e.g. the first interaction device is active for a given first orientation of the scanner and the second interaction device is active for a given second orientation of the scanner. Another way to achieve this is by coupling the two interaction devices to the scan workflow, such that e.g. the first interaction device is active for a first step of the scan workflow and the second interaction device is active for a second step of the scan workflow. Active may in this regard be understood as ready to receive an input from the user, such as a press, whereas deactivated may be understood as not being able to receive an input. An advantage of using two interaction devices, which are coupled, is that the user can initiate or stop the scanning regardless of how the scanner is oriented. If there is only one button for this purpose, the scanner may be held in a way where this button is facing away from the user e.g. towards the ground. This is in particular true when scanning the upper jaw of a patient, whereby it can become tricky to locate the button for initiating the scanning.

Thus, in some embodiments, the intraoral scanner further comprises a gyroscope configured to determine the orientation of the scanner. The first and second interaction devices may be interactively coupled to the gyroscope such that only one of said interaction devices is active at any given orientation of the scanner. The first interaction device may be configured to be active at a predefined first interval of orientations of the scanner, and the first interaction device may be configured to be inactive if the orientation of the scanner is outside the first interval.

Similarly, the second interaction device may be configured to be active at a predefined second interval of orientations of the scanner, and the second interaction device may be configured to be inactive if the orientation of the scanner is outside the second interval. The intraoral scanner may further comprise one or more light sources configured to indicate which of the first or second interaction device is active. As an example, each of the first and second interaction devices may be provided with a light source, such as an illumination ring, configured to indicate whether the given interaction device is active or inactive.

Navigation in GUI

In some embodiments, the 3D scanner system comprises a display. The display may be configured for displaying a rendering of the generated 3D representation of the scanned object(s), e.g. the scanned dental arch or teeth. Furthermore, a graphical user interface (GUI) may be provided by the display. The graphical user interface may contain a variety of menu options for the user to select. Some existing 3D scanners have a functionality wherein the scanner is used as a remote control, wherein the movements/orientation of the scanner can be used to highlight and select a menu item in the GUI. One or more motion sensors and/or gyroscopes may be located in the scanner to provide information on the movement and/or orientation of the scanner. However, some users may find these maneuvers impractical. The present disclosure suggests an alternative which may be used either as a replacement or as a supplement to existing ways of interacting with the GUI. One way is to use buttons on the scanner to navigate among the menu items. As an example, the interaction device may comprise five buttons, wherein one of said buttons is arranged in a center surrounded by four other buttons. The buttons may be mechanical buttons or touch sensitive buttons. The four other buttons may be arranged in a cross, wherein each button is provided with an arrow symbol. The button arranged in the center is preferably configured to select a highlighted menu item upon being pressed, and the other four buttons may be configured to navigate among menu items in the graphical user interface.

Reconfigurable Buttons

Figure 10:
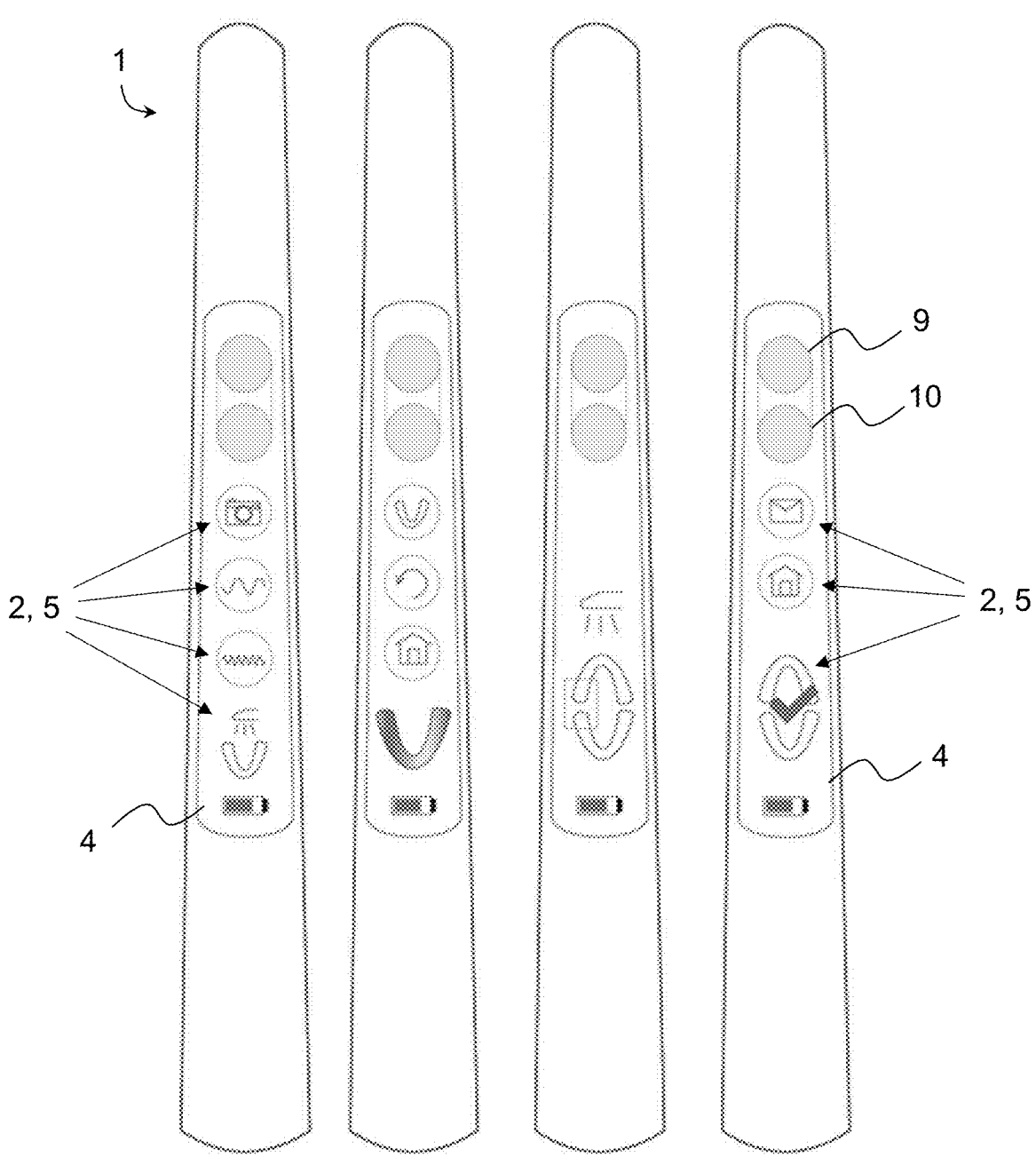
FIG. 10 shows four examples of how the icons presented in the electronic display on the scanner may change during the scan workflow.

In some embodiments, the 3D scanner system comprises one or more reconfigurable buttons. A reconfigurable button may be understood as a button which is configured for multiple purposes, wherein the button can be reconfigured into a specific purpose depending on the scan workflow and/or depending on where in the user interface, the user is. One way to achieve this is by combining a button or sensor with an electronic display, wherein the display is configured to provide an icon or text representing an action associated with pressing that button. An advantage hereof, is the ability to dynamically change the icon or text associated with the button depending on where in the scan workflow, the user is. This is illustrated in FIG. 10. Another advantage is that the same button can be used for a variety of different actions instead of needing one button for each action. The buttons may be covered by an electronic display, such as an LED display, OLED display, or an E-ink display. The electronic display may be the built-in display mentioned previously.

Thus, the physical buttons may not be visible from the outside; rather they may be realized using one or more force sensors or strain gauges positioned on the backside of the electronic display. The position of the force sensors may be indicated by icons, texts, or animations, generated by the display. The terms strain gauge sensor and strain gauge are used interchangeably herein.

Accordingly, in some embodiments, the reconfigurable buttons are based on strain gauge technology, preferably combined with the aforementioned display. Specifically, one way to construct the reconfigurable buttons is to mount/assemble one or more strain gauge sensors on a printed circuit board (PCB), wherein each strain gauge sensor is associated with a key or reconfigurable button. The PCB may be attached to a front layer, e.g. using an adhesive or tape. The front layer may be understood as the interaction layer, which is visible to the user. In preferred embodiments, an electronic display constitutes the front layer. The front layer may constitute a touch interface to the user. The strain gauge sensors are configured to detect and measure the strain in a material. Specifically, when pressing on an area above the strain gauge sensor, the material(s) underneath will mechanically deform on the microscale. The sensors are sensitive enough to detect and measure this deformation/strain in the material(s). One or more of the front layer, the PCB, and the force sensors themselves may deform once a user presses down on the front layer. The force sensors may be configured to output an analog signal, e.g. an analog voltage, when pressure is applied to the front layer. The analog signal may be converted to a digital signal using an analog-to-digital converter. The display and/or front layer may further be configured for receiving one or more touch gestures by the user, such as swiping gestures, pinching gestures, tapping gestures, or other gestures. The force sensors may be selected from the group of: Strain-gauge based force sensors, MEMS piezoresistive sensors, MEMS capacitive pressure sensors, optical pressure sensors, flexible thin-film force sensors, or piezoelectric force sensors.

The use of force sensors or strain gauge sensors has several advantages compared to e.g. capacitive touch sensing. One advantage is that they enable glove-sensitive operation, i.e. the user may interact with the reconfigurable buttons when wearing gloves. Conversely, a drawback of touchscreens based on capacitive sensing, is that the sensitivity is typically severely impaired by the use of gloves. In the use case of dentistry, the dentist typically wears gloves for hygienic reasons. Another advantage is that the strain gauge sensors are protected by the front layer, e.g. the electronic display and/or touch interface. Thus, the technology/arrangement may be utilized in wet conditions as well, which is also important in the typical use case in dental clinics. Yet another advantage is that the strain gauge sensors are pressure sensitive, i.e. they are preferably configured to detect not only a strain but the amount of strain, i.e. how hard a given key/button is pressed. This enables pressure dependent operations of the reconfigurable buttons.

The electronic display is preferably configured to change an icon, text, or animation in the display based on a progress or a specific step of the scan workflow. Specific steps of a typical scan workflow may include one or more of the following steps: scanning a lower jaw of the patient, scanning the upper jaw of the patient, scanning the natural bite of the patient, recording patient-specific motion, and viewing and/or manipulating the generated 3D representation. The scan workflow may comprise further steps in between the above mentioned steps. As an example, the scan workflow may enable the user to manipulate the 3D representation of the lower jaw before moving on to scanning the upper jaw.

An advantage on a scanner having reconfigurable buttons is that the same button may be utilized for many different operations or actions. Existing intraoral scanner typically feature one or more mechanical buttons, wherein each button has a single action associated with it. A disadvantage hereof, is that the user has to know what each button does. Furthermore, if one action is allocated per button, then many actions will imply that the scanner has many buttons on the surface. The reconfigurable buttons disclosed herein overcome these drawbacks. In particular, it is advantageous if the electronic display is configured to automatically change the user interface, e.g. one or more icons and/or texts in the display, wherein the change of the icons correlates with the scan workflow. This will ensure that the user is presented with the most relevant types of actions in a given step of the scan workflow. In other words, in some embodiments, the scanner system is configured to automatically change the associated action of a given reconfigurable button depending on the scan workflow, wherein the icon(s) and/or text(s) in the electronic display changes accordingly.

Figure 9:
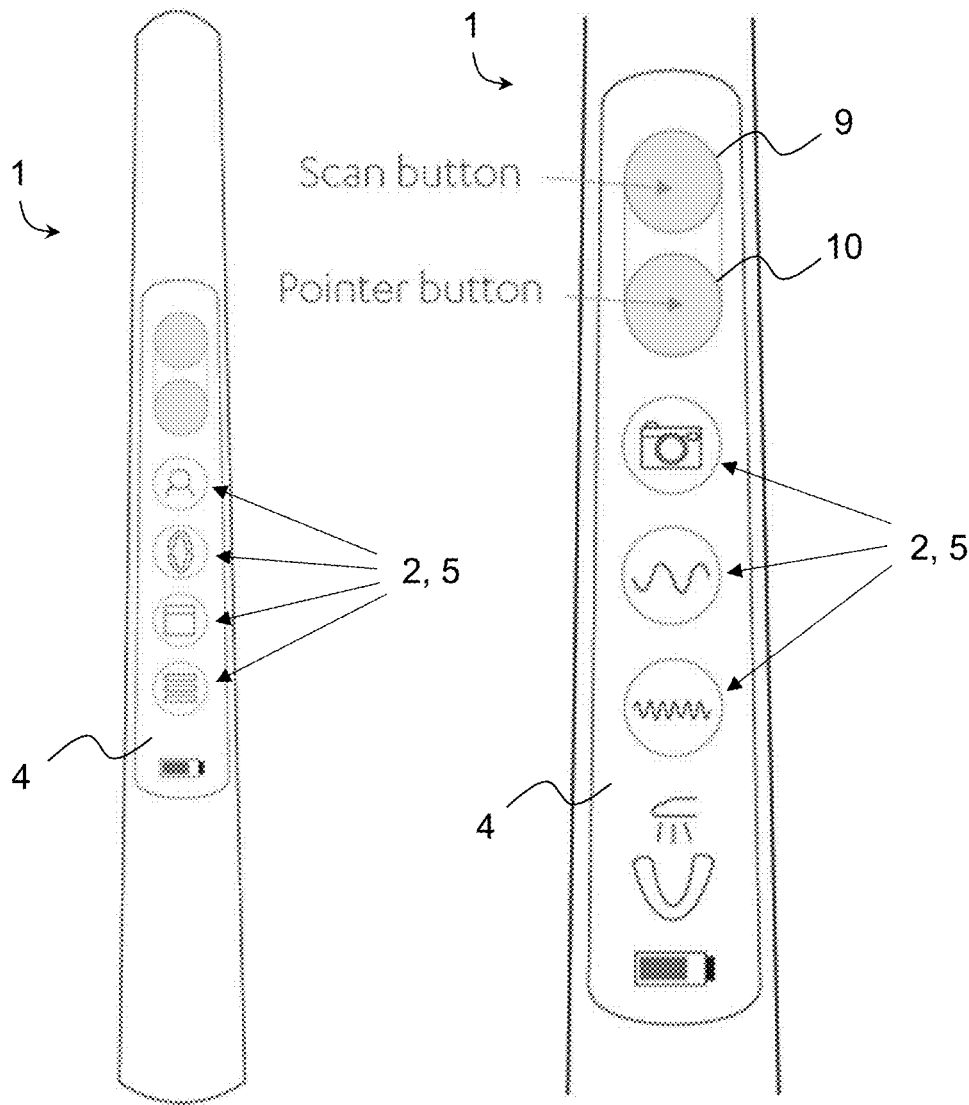
FIG. 9 shows an embodiment of an intraoral scanner, wherein the scanner comprises one or more reconfigurable buttons, wherein each button comprises a force sensor, such as a strain gauge sensor, wherein the sensors are covered by a front layer.

In some embodiments, the intraoral scanner comprises a plurality of reconfigurable buttons, such as two or more buttons, three or more buttons, four or more buttons, or five or more buttons. FIGS. 9-10 provide some examples. Preferably, the reconfigurable buttons are realized as described previously, i.e. where a strain gauge sensor is associated with each button, wherein an electronic display covers the sensors. Then, an icon or text representing an operation or action may be associated with each sensor, such that the number of icons displayed in the electronic display correspond to the number of sensors underneath the display. In some embodiments, a subset of the buttons is configured with a predetermined purpose, i.e. configured for a single action. As an example, one button may be dedicated as a 'scan button' configured to start/stop the scanning. Another button may be dedicated as a 'pointer button' configured to initiate a pointing operation, wherein the user may use the scanner as a pointer, wherein the orientation and/or movements of the scanner determines the location of the pointer on e.g. an external display, which may form part of the 3D scanner system. Thus, in some embodiments, only a subset of the buttons provided on the scanner are reconfigurable.

Figure 11:
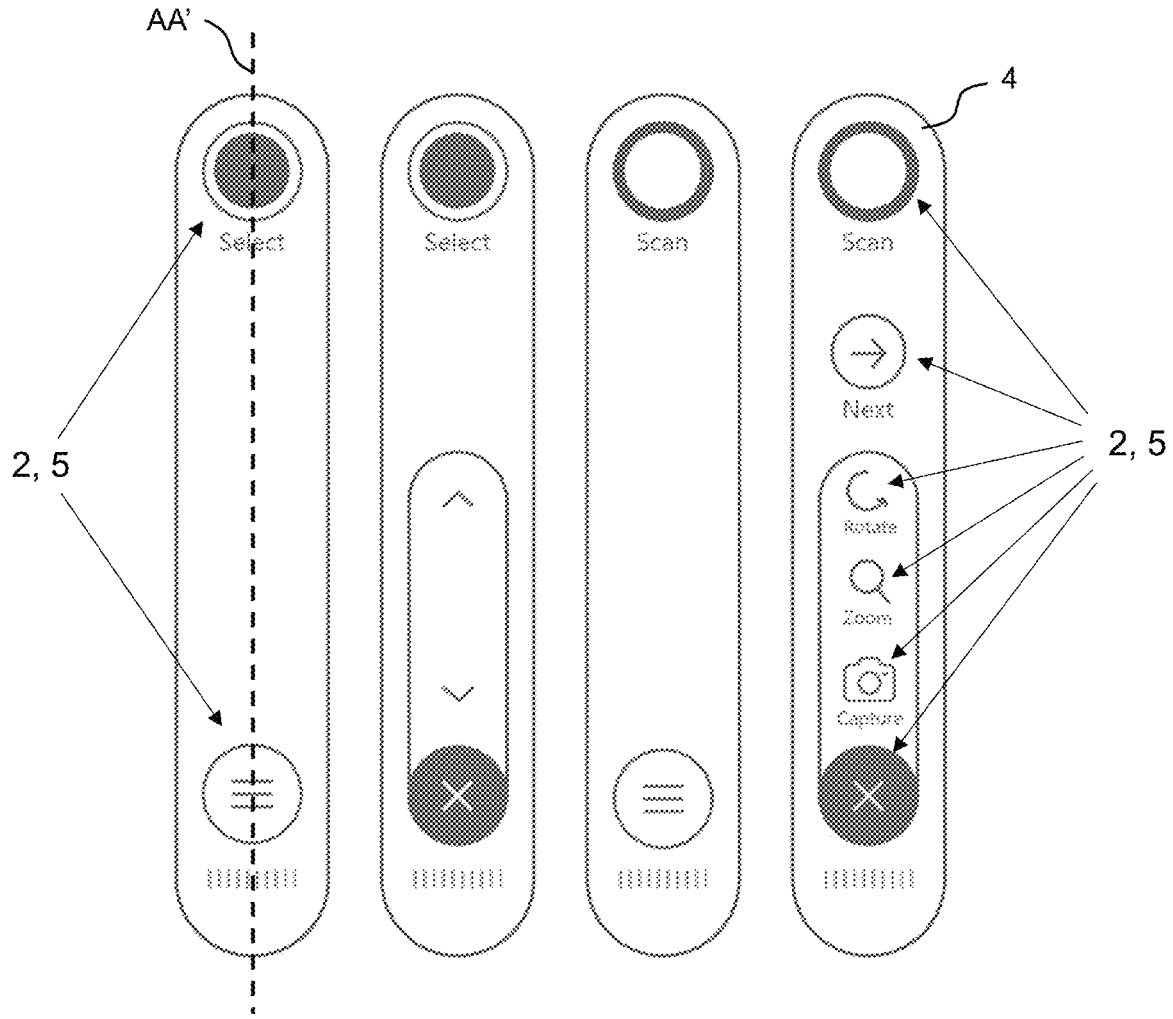
FIG. 11 shows an embodiment of an intraoral scanner, wherein the scanner comprises one or more reconfigurable buttons in combination with a display for displaying one or more icons.

In some cases, some of the reconfigurable buttons may become inactive in a specific step of the workflow. Then, the corresponding areas of the electronic display may be used for another purpose than displaying icon(s) or text(s) associated with those (inactive) button(s). This is also illustrated in FIGS. 10-11. Thus, the number of physical buttons (e.g. strain gauges) may be fixed throughout all four examples in FIG. 10 and FIG. 11; preferably only the icons are dynamically changed depending on what type of information is relevant to the user in a given step of the scan workflow.

DETAILED DESCRIPTION OF THE DRAWINGS

FIG. 1 shows an intraoral scanner 1 comprising an interaction device 8 (here exemplified as a button recessed in the surface) and a built-in display 4, such as an LED display. The button may be configured to start/stop the scanning and the built-in display 4 may be configured to display information relevant to the scan workflow. As an example, the built-in display 4 may show a simplified 2D visualization/illustration of one or more of the scanned dental arches. It may furthermore display other relevant information, such as the patient's name or the battery status. In this example, the user has scanned both dental arches (upper/lower), and both of them are visualized in the display 4. Thus, the scanning is completed. Each dental arch may be schematically illustrated by a plurality of dots or circles representing teeth (or other dental objects in the dental arch). The dots/circles may be colored differently depending on the amount and/or quality of the scan data generated for that particular dental object.

Figure 2:
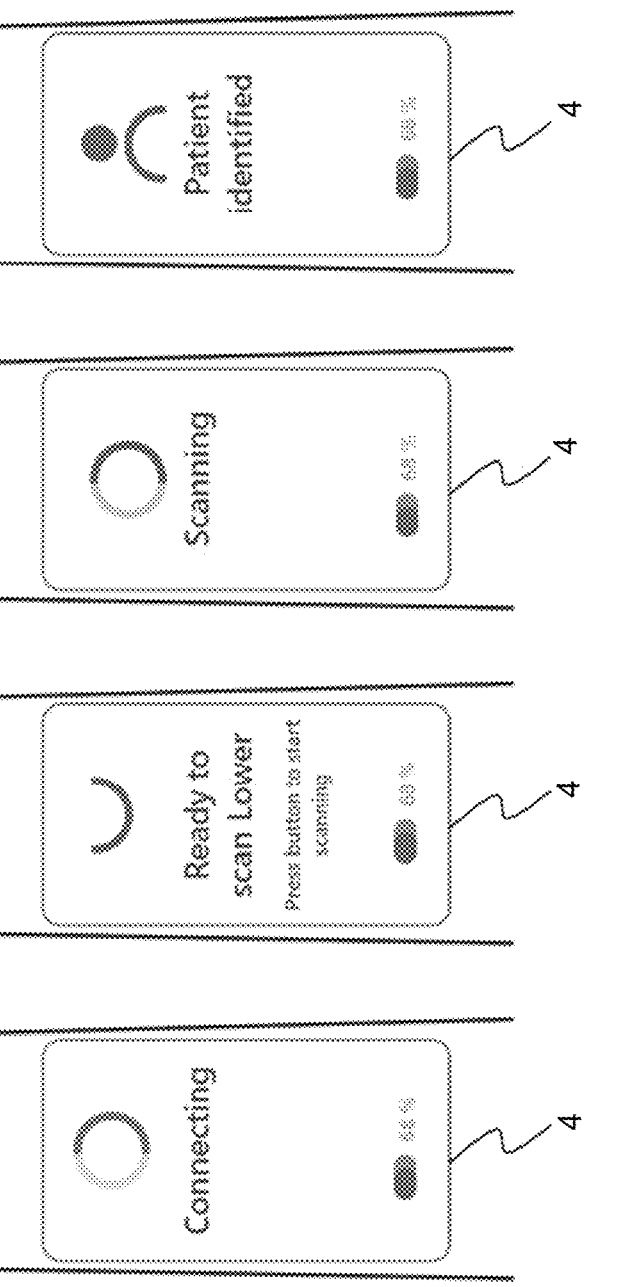
FIG. 2 shows an embodiment of an intraoral scanner with a built-in display, wherein four different examples of information in the display are shown.

FIG. 2 shows some examples of the kind of messages which could be displayed in the built-in display 4 of the intraoral scanner 1. For instance, the status of the scanner may be display, e.g. 'connecting', 'ready to scan lower', 'scanning', or 'patient identified'. The scanner 1 may be configured to automatically identify the patient based on comparing the scanned teeth with a previous 3D representation of that patient's teeth.

Figure 3:
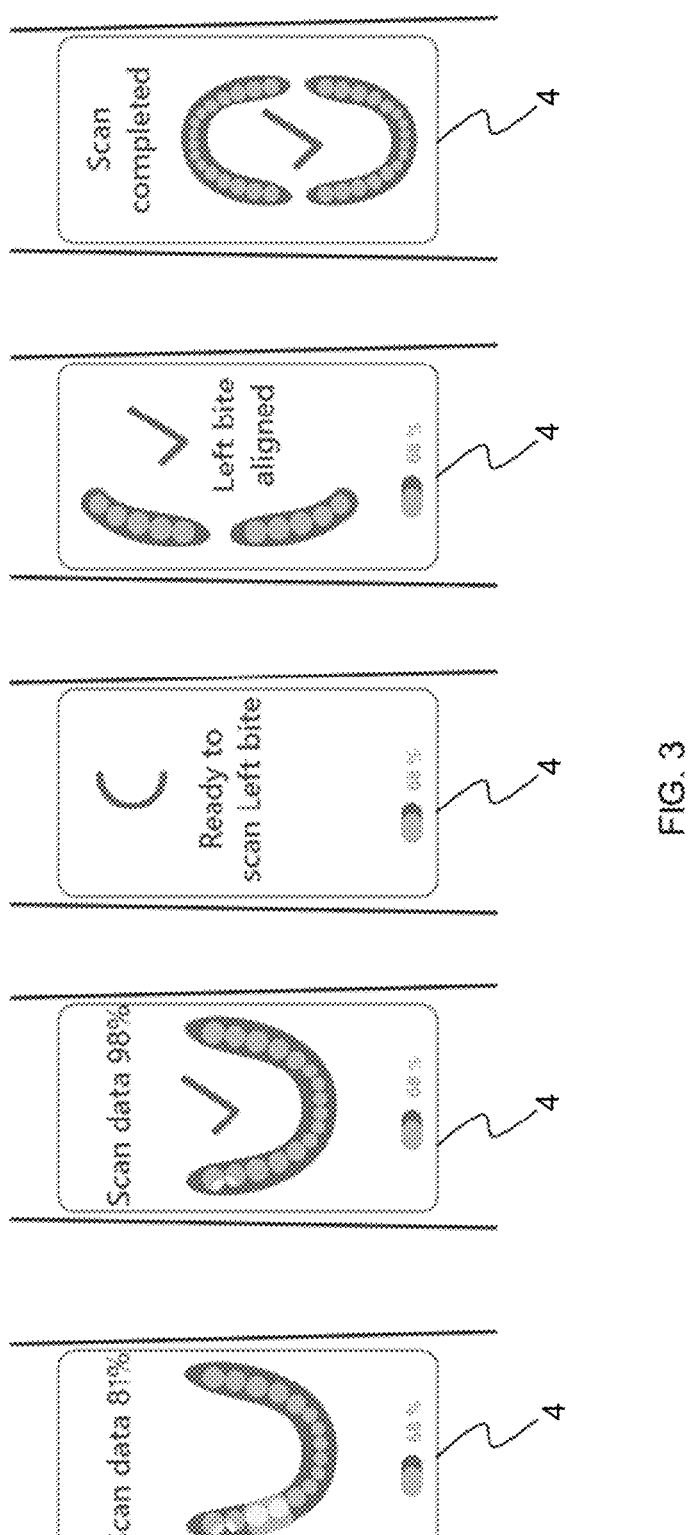
FIG. 3 shows an embodiment of an intraoral scanner with a built-in display, wherein a scan workflow is visualized in the display, wherein the progress of the workflow is shown.

FIG. 3 shows some more examples of what can be displayed in the display 4 of the scanner 1. In the left-most example, the user has scanned approximately 81% of a given dental arch, such as the lower jaw. The percentage may be reported directly as a number on the display, but it may additionally or alternatively be shown in the visualization of the dental arch, e.g. by filling in the dots/circles with a specific color, such as green. Alternatively, it may be that the dots/circles initially light up with a dim light, and then once scan data has been acquired for some areas, the dots/circles might appear with a more bright light for those areas. In the second example from the left, the user has scanned more of the patient's jaw and is ready to proceed in the scan workflow. However, the user is also informed of a particular area, such as a tooth, where scan data is insufficient, e.g. there might be missing data for this area. Then the user can choose to revisit that area and generate more scan data. Accordingly, the user is guided through the workflow and continuously informed of areas where the scanning can be improved with more data. The middle example shows a message of 'ready to scan left bite'. The fourth example from the left shows that the user has completed the step of scanning the patient's bite in the left side. Finally, the fifth example from the left shows that the scan is complete and uploaded, e.g. to a computer, server, or the cloud. In some embodiments, the visualization and information may be shown in a display, which is external to the scanner. The display may further be configured to display a graphical user interface.

FIG. 4 shows an example of how the visualization of a dental arch may be gradually built as scan data is generated for the dental arch. The visualization may be displayed in the built-in display 4 of the intraoral scanner 1 as previously mentioned. Alternatively or additionally, the visualization and information may be shown in a display, which is external to the scanner. The display 4 may further be configured to display a graphical user interface. One problem associated with initially displaying a full dental arch is that the scanner might not recognize exactly where in the patient's mouth the user initiates the scanning. As an example, a molar tooth may look similar in both sides of the dental arch. Therefore, in some embodiments, the processor(s) of the scanner system are configured to gradually generate the visualization, which is then continuously displayed in the built-in display 4 as scan data is captured and/or generated. As more scan data is acquired, eventually the scanner/processor(s) may be able to determine what areas of the patient's mouth the scanned areas correspond to. While scanning, the field of view may be indicated in the display 4, e.g. using a rectangle. In this example, the visualization of the dental arch is correlated with the local and global scan coverage measures as mentioned herein. For example, two or more colors may be used to indicate the local scan coverage, e.g. defined by one or more threshold values. If the local scan coverage is below a given threshold value, it is preferably indicated in the visualization e.g. using a predefined color, such as yellow. Conversely, if it is above a given threshold value, it may be colored using a second color, such as green. If the visualization is gradually built and in synchronization with the generation of the 3D representation, then it is also automatically correlated to the global scan coverage, since e.g. a half scanned arch will also only be displayed as a half arch in the display 4. However, the global scan coverage may also be reported as a number in the display 4 as mentioned before.

FIG. 5 shows an embodiment of an intraoral scanner 1 comprising a built-in display 4 configured to display a visualization of a dental arch. In this example, an outline of the dental arch including the teeth is shown even before scanning is initiated. Each tooth is symbolically illustrated by a shape such as a circle. The surrounding gingiva may similarly be shown schematically. Then, as the patient is being scanned, the outline of the visualization is gradually filled in e.g. using one or more colors, e.g. selected from a predefined color scheme. Thus, at least one purpose of the visualization is to schematically and visually display how much of the dental arch has been scanned, and preferably also if sufficient scan data has been generated for all areas. This may be displayed using different colors as previously explained. Therefore, the visualization does not need to be an accurate depiction of the patient's teeth. Rather, it serves as a feedback to the user on how the scanning progresses and what areas remain to be scanned.

FIG. 6 shows an embodiment of an intraoral scanner 1 comprising an interaction device 8 with one or more touch sensitive areas 11. In this example, the touch sensitive areas 11 constitute a touch sensitive ring with four mechanical buttons located beneath the ring. Two of said buttons are preferably configured to navigate back/forth in the scan workflow, i.e. change between scanning the upper/lower jaw or switching to a bite scan procedure. In this example, the scanner 1 is further provided with an illumination ring 6 surrounding at least a part of the interaction device. The illumination ring 6 may be configured such that e.g. a lower and/or upper part of the ring is correlated with scan data associated with a lower/upper jaw of the patient. In that way the user can easily verify or assess whether sufficient scan data has been obtained for both jaws/dental arches. The local/global scan coverage measures can be reported similarly as for the embodiments shown in FIGS. 4-5, i.e. using a predefined color scheme to provide an indication of the scan coverage. The left/right part of the illumination ring 6 may be associated with the bite scan procedure of the patient. These parts may partially overlap the upper and lower parts of the ring. The scanner 1 may be configured to provide a sound 12 once sufficient scan data has been acquired for a full dental arch or for a given bite scan. As an example, the sound 12 may be provided once a given part of the illumination ring 6 is colored fully green. When the scan workflow is entirely done, the illumination ring 6 may be fully lit in a predefined color, such as green.

FIG. 7 shows an embodiment of an intraoral scanner 1 comprising an illumination unit 7 for indicating which jaw/dental arch is being scanned. In this example, the illumination unit 7 comprises a plurality of individual light sources, such as LEDs, arranged along a curve on the scanner. As an example, the light sources may be arranged such that light emitted from the light sources glow through a transparent shell of the scanner around the circumference of the scanner. The light sources may be arranged on a given curve, such as an elliptical curve, around the scanner. The light sources may be configured with a similar purpose as previously described in relation to e.g. the illumination ring or the visualization of the dental arch. An advantage of an illumination unit 7 provided along a closed loop around the scanner is that it is visible also when the scanner is held upside down, e.g. when scanning the upper jaw. Thus, the user is preferably presented at all times with information of whether scan data is acquired/generated and if enough scan data has been acquired for a given area. Accordingly, the light sources of the illumination unit 7 may be correlated with the local and/or global scan coverage in a similar way as previously mentioned in relation to the other embodiments. In this embodiment, the intraoral scanner 1 further comprises an illumination symbol 13. The brightness and/or color of the illumination symbol 13 may be correlated with the generation of 3D scan data and/or correlated with the local/global scan coverage.

Figure 8:
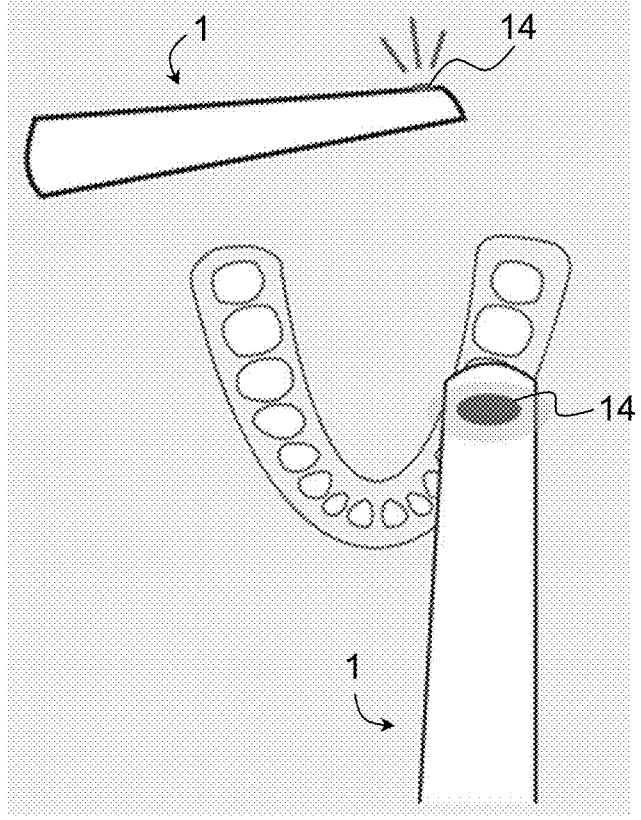
FIG. 8 shows an embodiment of an intraoral scanner, wherein the scanner comprises a light source configured to change illumination, brightness and/or color, wherein the change is correlated with the local scan coverage measure.

FIG. 8 shows an embodiment of an intraoral scanner 1, wherein the scanner 1 comprises a feedback light source 14. The feedback light source 14 is arranged such that light from it is visible on the outside of the scanner. As an example, the feedback light source 14 may be provided at the tip of the scanner or near the tip of the scanner, i.e. at the distal end of the scanner. The light source associated with the feedback light source 14 may be placed within the scanner, e.g. inside a shell of the scanner, but in that case the light should still be visible from the outside. One way to achieve this is to make the shell of the scanner transparent. The feedback light source 14 is preferably correlated with e.g. the local scan coverage, such that when enough scan data has been generated for a given dental object, the feedback light source 14 is either turned on or changes color or brightness, or combinations thereof. As an example, the feedback light source 14 may be green if the local scan coverage is above a predefined threshold value.

FIG. 9 shows an embodiment of an intraoral scanner 1, wherein the scanner comprises one or more reconfigurable buttons 2, wherein each button comprises a strain gauge sensor, wherein the sensors are covered by a front layer. In this embodiment, an electronic display 4, such as an LED display, is used as the front layer. In this example, two buttons (9, 10) are configured with a predetermined fixed purpose, such as initiating the scanning or initiating a pointer operation. All of the buttons shown (2, 9, 10) may be based on the same force sensor technology, wherein force sensors are covered by a display 4. The left example shows a scanner with four reconfigurable buttons 2, wherein the scanner is configured to automatically change the icon 5 and associated action of each button 2 depending on where in the scan workflow, the user is. The right example shows a scanner 1 with three reconfigurable buttons 2, wherein the display 4 is used to display further information relating to the scanning e.g. the scanning mode and/or a visualization of the dental arch. In this example, one of the reconfigurable buttons 2 may be configured to acquire a screenshot of the 3D representation. Another button may be configured to change colors on the 3D representation, e.g. from normal colors to fluorescence colors.

FIG. 10 shows an embodiment of an intraoral scanner 1, wherein the scanner 1 comprises one or more reconfigurable buttons 2, wherein each button 2 comprises a strain gauge sensor, wherein the sensors are covered by a front layer. In this embodiment, an electronic display 4, such as an LED display, is used as the front layer. In the figure, four different examples are given, wherein each example may correspond to a given step of the scan workflow. Thus, the user may be presented with different options depending on where in the scan workflow, the user is. The scanner 1 may be configured to provide haptic feedback correlated with a selection made by the user, i.e. the scanner may provide a vibration when the user touches or presses an icon 5 in the display 4.

Figure 12:
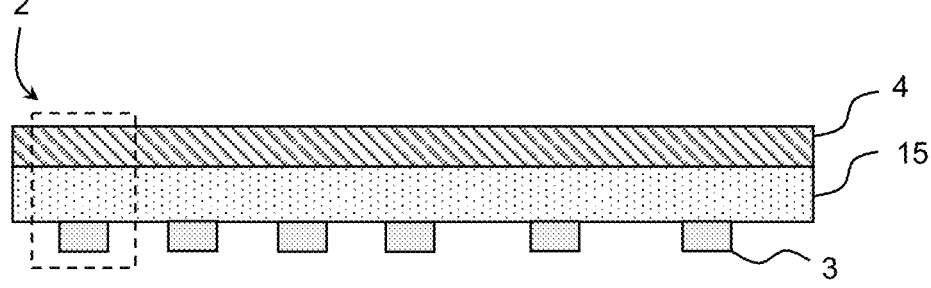
FIG. 12 shows a cross-sectional view of an array of reconfigurable buttons based on force sensors, such as strain gauge sensors, wherein a display covers the force sensors.

FIG. 11 shows an example of a user interface for an intraoral scanner 1. In this embodiment, the intraoral scanner 1 comprises one or more reconfigurable buttons 2, wherein each button comprises a strain gauge sensor, wherein the sensors are covered by a front layer. In this embodiment, an electronic display 4, such as an LED display, is used as the front layer. Accordingly, the intraoral scanner 1 may comprise a built-in display 4 with one or more strain gauge sensors/forces sensors arranged below the display 4, wherein the forces sensors are sensitive to touches and/or presses on the display 4. A cross-sectional view along the line AA' is shown in FIG. 12. Notice that even though only two icons 5 appear in the display in the left-most example, there may be several strain gauge sensors 3 arranged below the display 4 as shown in FIG. 12. In some cases, only a subset of these force sensors is active at a given time, e.g. depending on where in the scan workflow the user is; compare e.g. the left-most example to the right-most example. As an example, a first reconfigurable button 2 may be configured as a 'select button' in some parts of the scan workflow (two left examples) and the same reconfigurable button 2 may be reconfigured into a 'scan button' in other parts of the scan workflow. The reconfigurable buttons 2 may be automatically reconfigured depending on the choices made by the user (e.g. depending on the user selection), and/or they may be automatically reconfigured depending on the progress/specific step of the scan workflow.

Furthermore, in this embodiment a second reconfigurable button 2 may be configured to toggle a menu or navigation bar. The second reconfigurable button 2 may be associated with a 'collapsed menu icon', sometimes also referred to as a hamburger button. The 'collapsed menu icon' may be displayed in the display 4 on the scanner 1. Once a user presses the second reconfigurable button 2, one or more icons 5, e.g. scroll bars or menu options, may appear in the display 4. A user may interact with these new icons/options by touching or pressing the display on the icons, or by e.g. a scrolling motion in case of a scroll bar. This may be facilitated by the use of one or more strain gauges 3 below the display 4. An advantage of using these instead of capacitive sensing is that they can be used even when the user wears gloves. Furthermore, capacitive sensing is sensitive to e.g. water droplets, thus making it difficult to operate in wet conditions. The scanner 1 may be configured to provide haptic feedback upon the user pressing/touching the icons 5 in the display 4.

Figure 22:
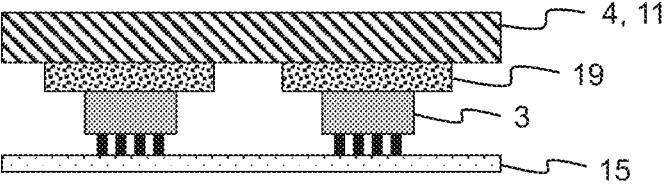
FIG. 22 shows a cross-sectional view of an array of reconfigurable buttons based on force sensors, wherein a display covers the force sensors.

FIG. 12 shows a cross-sectional view of an array of reconfigurable buttons 2 based on strain gauge sensors 3, wherein a display 4 covers the strain gauge sensors 3. The strain gauge sensors 3 may be arranged on a printed circuit board 15 (PCB) or another suitable carrier. The printed circuit board/carrier 15 may be attached to the display 4 using adhesive such as adhesive tape e.g. in the form of double-sided tape (not shown in the figure). Thus, in some embodiments, the sensors 3 are suspended from the display 4. In other embodiments, an intermediate layer (different from the PCB) is placed between each sensor and the display. The intermediate layer may be made from an elastic material such as polyurethane, silicone, or rubber. The intermediate layer may be attached to the lower side of the display using an adhesive, such as a pressure-sensitive adhesive. Such an example is shown in FIG. 22. In the example of FIG. 12, six reconfigurable buttons 3 are shown. However, it should be appreciated that other numbers and arrangements of reconfigurable buttons 3 may be envisioned without departing from the scope of the present disclosure. The cross-sectional view may correspond to a cross-sectional view taken along the line AA' in FIG. 11. It should be noted that FIG. 12 only shows a schematical cross-sectional view; thus, the dimensions of e.g. the layers are not proportional/to scale.

FIG. 13 shows an example of how the dental arch may be visualized in the built-in display. The visualization may be gradually generated during the scanning session as scan data is generated. The visualization may be in the form of a sketch/illustration serving the main purpose of showing the user how much of the dental arch has been scanned and if some areas need further scanning. Thus, the visualization can be a simple illustration in contrast to a realistic rendering of the patient's actual teeth. This has the advantage of lowering the demands to the hardware such as the processing power and the specifications of the display.

Accordingly, the cost of the electronic components can be reduced by making a more simple illustration or sketch of the dental arch. In this example, the visualization may be made in grey-scale during scanning. Once the scanning is paused or stopped, the visualization may change colors into a color scheme correlated with the local/global scan coverage value(s). Specifically, if some teeth have not been fully imaged, e.g. if one side of the teeth needs further scanning, then the edge/boundary of the teeth may be highlighted in the visualization e.g. using a specific color. In general it is desired if any part of the teeth which lacks scan data, i.e. with a corresponding low local scan value, is highlighted in the visualization. This allows the user to revisit those areas with the scanner and generate scan data for those areas. The previously mentioned colors scheme of yellow/green may be utilized, e.g. in the form of a color gradient.

Figure 14:
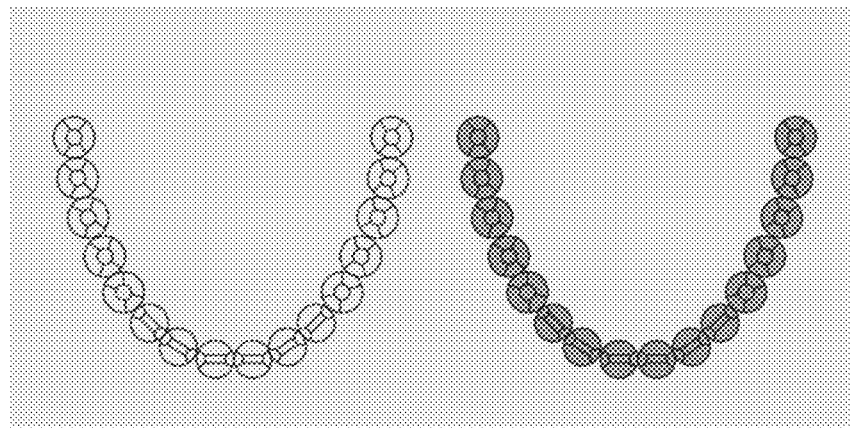
FIG. 14 shows another example of how the dental arch may be visualized in the built-in display.

FIG. 14 shows another example of how the dental arch may be visualized in the built-in display. In this example, each tooth in the dental arch is schematically visualized using five connected surfaces. The five surfaces may correspond to the occlusal, buccal, lingual, mesial, and distal surfaces of a tooth. The five surfaces may be colored in a color scheme correlated with the local scan coverage, i.e. each surface may be individually colored e.g. using a color gradient to reflect the scan coverage of that surface. This will enable the user to clearly see which surface of the tooth/teeth that needs additional imaging/scanning. In the left example, all of the teeth are grey, since scanning has not been initiated. In the right example, all the teeth including all surfaces are colored using the same color, e.g. green, to show that sufficient scan data has been generated for all teeth in the dental arch.

Figure 15:
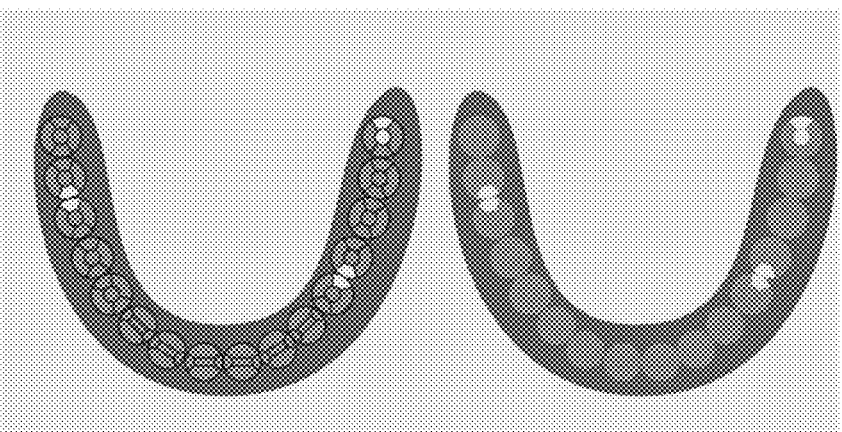
FIG. 15 shows yet another example of how the dental arch may be visualized in the built-in display.

FIG. 15 shows yet another example of how the dental arch may be visualized in the display. This example is largely similar to the example shown in FIG. 14. However, in this example, the gingiva surrounding the teeth is also visualized. Any of the gingiva and/or the teeth may be colored in a color scheme correlated with the local scan coverage. This example shows how it may look in the visualization if one or more surfaces of the teeth have a low scan coverage value, i.e. surfaces that optimally need additional imaging/scanning. These surfaces are highlighted in the visualization; here shown as light-grey or yellow. This visualization has the advantage that the user is informed not only which teeth need to be scanned further, but also which specific surfaces of the teeth (occlusal, buccal, lingual, mesial, and/or distal) lacks scan data. Therefore, the user is visually guided to the areas that needs extra attention.

Figures 16, 17, 18:
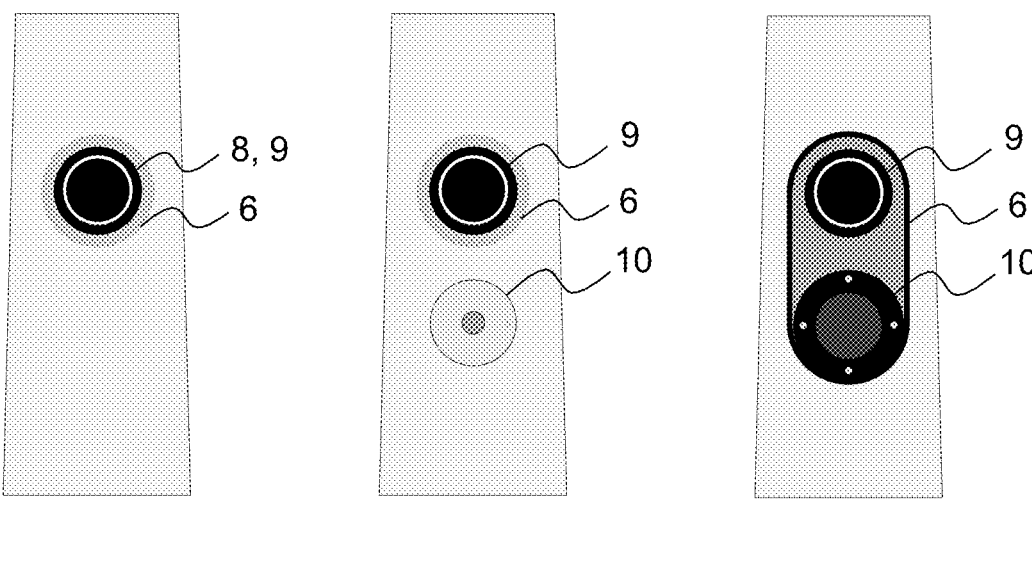
FIG. 16 shows an embodiment of an interaction device configured for initiating an action upon activation. The interaction device is located in an intraoral scanner (not fully shown).
FIG. 17 shows an embodiment of an intraoral scanner comprising two interaction devices. The first interaction device may be similar to the one described in relation to FIG. 16.
FIG. 18 shows another embodiment of an intraoral scanner comprising two interaction devices. The first interaction device may be similar to the one described in relation to FIG. 16.

FIG. 16 shows an embodiment of an interaction device 8 configured for initiating an action upon activation. The interaction device 8 is located in an intraoral scanner (not fully shown). In this embodiment, the intraoral scanner further comprises an illumination ring 6 located along the circumference of the interaction device 8. In this example, the interaction device 8 may be a single button, such as a mechanical button, or a touch sensitive area, wherein the interaction device is configured for initiating and/or pausing/stopping a given scanning operation, i.e. in order to start/stop the acquisition of 3D scan data.

FIG. 17 shows an embodiment of an intraoral scanner comprising two interaction devices (9, 10). The first interaction device 9 may be similar to the one described in relation to FIG. 16. The second interaction device 10 (e.g. located beneath the first one), may be a touch sensitive area or button, configured for being used as a pointer button. Thus, the pointer button may be configured to initiate a pointing operation, wherein the user may use the scanner as a pointer, wherein the orientation and/or movements of the scanner determines the location of the pointer e.g. on an external display. Alternatively, the second interaction device 10 may be configured for pointing operations similar to a touchpad or pointing stick, wherein a pointer on an external display is controlled by finger movements on the second interaction device 10. Advantageously, the two interaction devices (9, 10) may be tactile different such that they can be easily distinguished by the user. As an example, the pointer button may be indented in the surface of the scanner. As another example, the two interaction devices (9, 10) may have different surface shapes in order to be distinguished. One of the two interaction devices (9, 10) may be provided with a small knob or protrusion, such that the tactility of the two devices (9, 10) is different, whereby the user can feel the difference. The scanner may further be configured to provide a haptic feedback in response to the pointing operation(s) performed by the user.

FIG. 18 shows an embodiment of an intraoral scanner comprising two interaction devices (9, 10). The first interaction device 9 may be similar to the one described in relation to FIG. 16. The second interaction device 10 (e.g. located beneath the first one), may comprise one or more buttons and/or touch sensitive areas, e.g. embodied as a touch sensitive pad. As an example, the second interaction device 10 may comprise five mechanical buttons and one or more touch sensitive areas. The touch sensitive pad may be curved such that it follows the curvature of the body/housing/shell of the scanner. In this embodiment, the second interaction device 10 is configured for navigating through options in a graphical user interface during a workflow; thus, the user can cycle through the options rather than pointing on a specific option in the user interface. This has the advantage that the user need not point the scanner in any specific direction for choosing an option. Furthermore, the option may be highlighted on the display, e.g. using an outline around the given option, whereby the user is informed of the currently highlighted options before selecting said option. The touch sensitive pad may further be configured for swiping operations. In this embodiment, the illumination ring 6 is arranged such that it surrounds both interaction devices (9, 10), whereby an elongated illumination is provided. Alternatively, the illumination ring 6 can be provided around only one of the interaction devices (9, 10), e.g. around the top button 9, the 'scan button' configured for initiating and/or pausing the acquisition of 3D data.

Figure 19:
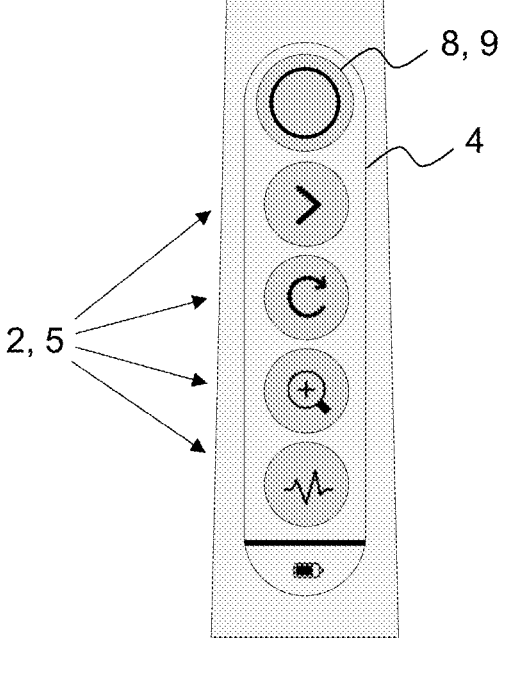
FIG. 19 shows an embodiment of an intraoral scanner comprising one or more reconfigurable buttons.

FIG. 19 shows an embodiment of an intraoral scanner comprising one or more reconfigurable buttons 2, and a display 4 configured for displaying one or more icons 5 associated with the reconfigurable buttons 2. The reconfigurable buttons 2 may be realized by utilizing one or more strain gauge sensors or force sensors located beneath the display 4 as explained elsewhere herein, such as in relation to FIGS. 11-12. The display 4 may be a light-emitting diode (LED) display, an organic LED (OLED) displays, a liquid-crystal display (LCD) display, an electronic ink (E Ink) displays, or other suitable displays. The scanner may be configured to automatically change one or more icons or texts 5 associated with the reconfigurable buttons 2 according to the options relevant for a particular step or mode in a given scanning workflow/scanning session. Thus, the scanner may be configured to reconfigure one or more of the buttons 2 in response to the options available in the user interface for a given mode or workflow or in response to a given selected option. The relevant workflow may be any workflow forming part of the software associated with the 3D scanner system, such as a scan workflow or a diagnostic workflow. Accordingly, both the functionality and the icon 5 of a given reconfigurable button 2 are preferably automatically changed by the scanner. The icons or texts 5 (and associated functionality) on the scanner may be changed in accordance with the icons or texts provided in the user interface on the display. In some cases, the scanner system is configured such that the user can set up his own choice of functionality for the reconfigurable buttons 2. The reconfigurable buttons 2 may be indented in the surface of the scanner. In this example, the scanner comprises a first interaction device 9, e.g. a mechanical button for initiating a scan, and four reconfigurable buttons 2. Other combinations and number of buttons can be envisioned without departing from the scope of the disclosure. The scanner may further comprise one or more light sources, e.g. embodied as a thin strip of light, e.g. configured with the purpose of indicating connectivity of the scanner to an external device such as a computer. Alternatively, the display 4 of the scanner may be configured for displaying such a strip of light. The scanner may further comprise an icon for indicating battery status, e.g. shown in the display.

Figure 20:
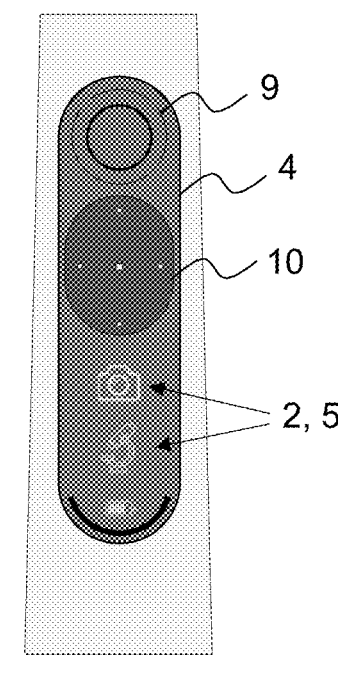
FIG. 20 shows another embodiment of an intraoral scanner comprising one or more reconfigurable buttons.

FIG. 20 shows an embodiment of an intraoral scanner comprising one or more reconfigurable buttons 2, and a display 4 configured for displaying one or more icons 5 associated with the reconfigurable buttons 2. In this embodiment, the scanner comprises one button 9 configured as a 'scan button', i.e. configured for initiating and/or pausing/stopping a scan. The scanner further comprises a second interaction device 10, here embodied as a touch sensitive pad or 'mouse pad' having two or more directional buttons, such as four directional buttons, and a central button for selection. The touch sensitive pad may further be configured for swiping operations. The touch sensitive pad may be curved such that it follows the curvature of the outer surface of the scanner. The scanner further comprises two reconfigurable buttons 2 which can be customized or reconfigured according to a desired action/option. Similar to the embodiment of FIG. 19, the display 4 of the scanner may be configured for displaying a light strip for indicating connectivity. The scanner may further comprise an icon for indicating battery status, e.g. shown in the display 4.

Figure 21:
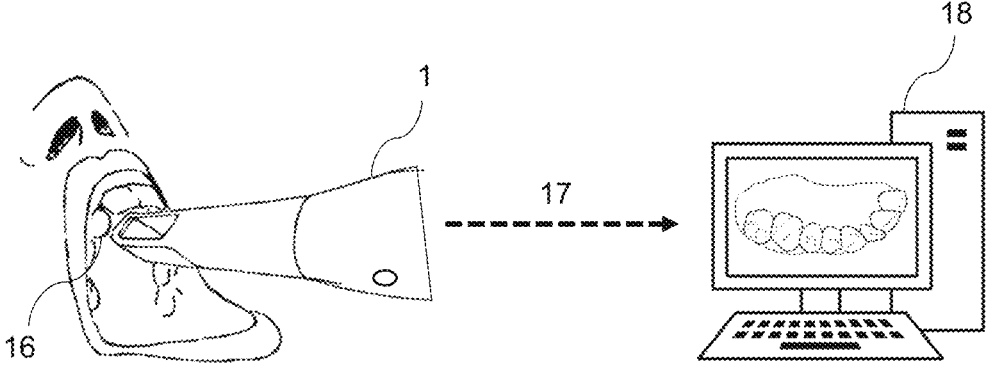
FIG. 21 shows an embodiment of a 3D scanner system according to the present disclosure.

FIG. 21 shows an embodiment of a 3D scanner system according to the present disclosure. The 3D scanner system may comprise an intraoral scanner 1 for acquiring images and/or 3D frames inside the oral cavity of a subject. In particular, the intraoral scanner 1 may be configured for acquiring images and/or 3D frames of at least a part of the dental arch 16 of the subject. The intraoral scanner 1 may be configured for transmitting the images and/or 3D frames to a computer system 18. The data transmission 17 may be performed wirelessly or using a cable, such as an ethernet cable, USB cable, or similar. The computer system 18 may be configured for generating a digital 3D model of the scanned object, such as the dental arch 16, and it may further be configured for displaying the 3D model on a display.

FIG. 22 shows a cross-sectional view of an array of reconfigurable buttons 2 based on force sensors 3, wherein a display 4 covers the force sensors 3. In this embodiment, there is an intermediate layer 19 located between the display 4 and each sensor 3. The intermediate layer 19 may advantageously be made from an elastic material such as polyurethane, silicone, or rubber. Other elastic materials can be envisioned. The intermediate layer 19 may be attached to the lower side of the display 4 using an adhesive. Each sensor 3 may be connected to a printed circuit board (PCB) 15 for reading out each sensor. The intermediate layer 19 may ensure that each sensor 3 can be pre-loaded, in particular if the PCB 15 is in contact with another surface, such as a side wall of the housing of the scanner. In this embodiment, two reconfigurable buttons are shown. However, it should be appreciated that other numbers and arrangements of reconfigurable buttons may be envisioned without departing from the scope of the present disclosure.

FURTHER DETAILS OF THE INVENTION

1. A 3D scanner system for scanning a dental arch inside an oral cavity of a patient during a scanning session, the scanner system comprising:
   an intraoral scanner; and
   one or more processors configured to generate 3D scan data of at least a part of the dental arch.
2. A 3D scanner system according to item 1, wherein the intraoral scanner is a handheld intraoral scanner.
3. A 3D scanner system according to any of the preceding items, wherein the intraoral scanner comprises an interaction device configured for initiating an action upon activation.
4. A 3D scanner system according to any of the preceding items, wherein the generation of 3D scan data is performed continuously during the scanning session.
5. A 3D scanner system according to any of the preceding items, wherein the one or more processors are configured for automatically identifying the patient based on comparing the 3D scan data with previously obtained 3D scan data of the same patient or by comparing with generic 3D scan data.
6. A 3D scanner system according to any of the preceding items, wherein the dental arch comprises one or more dental objects selected from the group of: teeth, dental restorations, tooth preparations, missing teeth, gingiva.
7. A 3D scanner system according to any of the preceding items, wherein the one or more processors are configured for generating a 3D representation of the scanned part(s) of the dental arch based on the 3D scan data.
8. A 3D scanner system according to any of the preceding items, wherein the one or more processors are configured for determining a global scan coverage measure based on whether the dental object(s) in the dental arch is sufficiently covered by the generated 3D scan data.

9. A 3D scanner system according to item 8, wherein the global scan coverage measure is based on the size of the 3D representation, such as total surface area of the 3D representation.
10. A 3D scanner system according to any of the items 8-9, wherein the global scan coverage measure is based on the amount and/or density of 3D scan data generated for the dental arch.
11. A 3D scanner system according to any of the preceding items, wherein the one or more processors are configured for determining a local scan coverage measure based on whether a given dental object in the dental arch is sufficiently covered by the generated 3D scan data.
12. A 3D scanner system according to item 11, wherein the local scan coverage measure is based on the density of the generated 3D scan data.
13. A 3D scanner system according to item 12, wherein the 3D scan data is in the form of point clouds or meshes.
14. A 3D scanner system according to any of the items 12-13, wherein the density is measured in number of data points per area or volume.
15. A 3D scanner system according to any of the items 11-14, wherein the local scan coverage measure is based on the amount and/or density of 3D scan data generated for a given dental object in the dental arch.
16. A 3D scanner system according to any of the items 8-15, wherein the system is configured to visualize the local/global scan coverage measure.
17. A 3D scanner system according to any of the items 8-16, wherein the system further comprises a feedback light source, such as an LED, located on the intraoral scanner, wherein the feedback light source is configured to change illumination, brightness and/or color, wherein the change is correlated with the local and/or global scan coverage measure.
18. A 3D scanner system according to item 17, wherein the feedback light source is configured to light up, and/or change brightness, and/or change color when the local scan coverage measure reaches a predefined threshold value, such that the intraoral scanner signals whether enough 3D scan data has been obtained for a given dental object.
19. A 3D scanner system according to any of the items 17-18, wherein the feedback light source is configured to change color based on detection of caries.
20. A 3D scanner system according to any of the preceding items, wherein the action is selected from the group of: initiating the scanning session, stopping the scanning session, pausing the scanning session, resuming the scanning session, or selecting a menu option.
21. A 3D scanner system according to any of the preceding items, wherein the interaction device comprises one or more mechanical buttons.
22. A 3D scanner system according to any of the preceding items, wherein at least one of the mechanical buttons is recessed in a surface of the intraoral scanner.
23. A 3D scanner system according to any of the preceding items, wherein the system further comprises a display for displaying a visualization of the dental arch.
24. A 3D scanner system according to any of the items 21-23, wherein the interaction device comprises five buttons, such as mechanical buttons, wherein one of said buttons is arranged in a center surrounded by four other buttons.
25. A 3D scanner system according to any of the items 21-24, wherein the button arranged in the center is configured to select a highlighted menu item upon being pressed, and wherein the other four buttons are configured to navigate among menu items in a graphical user interface.

26. A 3D scanner system according to any of the items 21-25, wherein the graphical user interface is provided by a display.

27. A 3D scanner system according to any of the preceding items, wherein the interaction device comprises one or more touch sensitive areas configured for detecting an input from a user based on capacitive sensing or force touch technology.

28. A 3D scanner system according to item 27, wherein the interaction device further comprises at least four mechanical buttons located beneath the touch sensitive area(s).

29. A 3D scanner system according to item 28, wherein a first mechanical button is configured to, upon activation, proceed to a next step in the scanning session, and wherein a second mechanical button is configured to, upon activation, proceed to a previous step in the scanning session.

30. A 3D scanner system according to any of the preceding items, wherein the intraoral scanner comprises a touch sensitive ring comprising two or more touch sensitive areas configured for detecting an input from a user, wherein the touch sensitive ring is based on force touch technology.

31. A 3D scanner system according to any of the items 27-29, wherein the intraoral scanner further comprises an illumination ring, such as a light-emitting diode (LED) ring, which is located along the circumference of the touch sensitive areas.

32. A 3D scanner system according to item 31, wherein the illumination ring is configured to display a visualization of the dental arch being scanned, wherein the illumination ring is further configured to visualize a progress of the scanning session.

33. A 3D scanner system according to any of the preceding items, wherein the dental arch is a lower arch (mandibular) or an upper arch (maxilla) of the patient.

34. A 3D scanner system according to any of the items 31-33, wherein a first part of the illumination ring is configured for displaying information related to a lower arch of the patient, and wherein a second part of the illumination ring is configured for displaying information related to an upper arch of the patient.

35. A 3D scanner system according to any of the items 31-34, wherein a third and/or fourth part of the illumination ring is configured for displaying information related to a bite scan procedure within the scanning session.

36. A 3D scanner system according to item 35, wherein the third and fourth parts are opposite to each other and wherein the third or fourth part is used to display information related to a left or right bite scan procedure.

37. A 3D scanner system according to any of the items 35-36, wherein the third and/or fourth parts overlaps the first and/or second part of the illumination ring.

38. A 3D scanner system according to any of the items 31-37, wherein the information includes a scan coverage measure, such that the illumination ring is configured to visualize the part(s) of the upper/lower arch which has been scanned, i.e. for which 3D scan data has been acquired.

39. A 3D scanner system according to any of the items 31-38, wherein the illumination ring is configured to be fully lit with a predefined color, such as green, once the scanning session is completed.

40. A 3D scanner system according to any of the preceding items, wherein the intraoral scanner further comprises a built-in display configured to display information related to the scanning session.

41. A 3D scanner system according to item 40, wherein the built-in display is configured to display a visualization of the dental arch being scanned.

42. A 3D scanner system according to item 41, wherein the visualization of the dental arch is continuously generated and/or gradually expanded during the scanning session based on the scanned parts of the dental arch.

43. A 3D scanner system according to any of the items 41-42, wherein the scanner system is configured to continuously generate and/or expand the visualization of the dental arch during the scanning session based on the scanned parts of the dental arch.

44. A 3D scanner system according to any of the items 41-43, wherein the visualization only includes parts of the dental arch for which 3D scan data exist.

45. A 3D scanner system according to any of the items 41-44, wherein dental objects, such as teeth, are indicated or symbolically visualized in the visualization of the dental arch.

46. A 3D scanner system according to any of the items 40-45, wherein the built-in display is further configured to visualize a progress of the scanning session.

47. A 3D scanner system according to item 46, wherein the built-in display is configured to show the progress as a percentage score.

48. A 3D scanner system according to any of the items 40-47, wherein the built-in display is a color display, such as an LED display.

49. A 3D scanner system according to any of the items 40-48, wherein the visualization of the dental arch being scanned is updated continuously during the scanning session, and wherein the update of the visualization is correlated with the generated 3D scan data.

50. A 3D scanner system according to any of the items 40-49, wherein the built-in display is configured to show the progress by illuminating or changing the color of a part of the visualization of the dental arch, such that part(s) which have been scanned are illuminated and/or colored differently than part(s) for which no or insufficient 3D scan data has been acquired during the scanning session.

51. A 3D scanner system according to any of the items 40-49, wherein the scanner is configured to color the visualization using a color gradient correlated with the local scan coverage measure, such that part(s) which have been scanned are colored differently than part(s) for which no or insufficient 3D scan data has been generated during the scanning session.

52. A 3D scanner system according to any of the items 40-51, wherein the dental arch comprises one or more dental objects, and wherein the built-in display is configured to visualize the dental objects as individual symbols in the visualization of the dental arch.

53. A 3D scanner system according to any of the items 40-52, wherein the display is configured to schematically visualize each dental object in the dental arch using five connected surfaces corresponding to the occlusal, buccal, lingual, mesial, and distal surfaces of a tooth.

54. A 3D scanner system according to any of the items 52-53, wherein the built-in display is configured to show the progress by illuminating and/or changing the color of the individual symbols based on the generated 3D scan data, such that dental objects which have been scanned are illuminated and/or colored differently than dental objects which have not been scanned or for which insufficient scan data has been acquired.

55. A 3D scanner system according to any of the items 40-54, wherein the built-in display is configured to show a status of the intraoral scanner, wherein the status is selected from the group of: connecting, ready to scan, ready to scan lower arch, ready to scan upper arch, ready to scan left bite, ready to scan right bite, scanning, patient identified, scanning complete, scan uploaded, and/or combinations thereof.

56. A 3D scanner system according to any of the preceding items, wherein the intraoral scanner further comprises an illumination unit which is integrated in the intraoral scanner.

57. A 3D scanner system according to item 56, wherein the illumination unit is configured to provide illumination along at least a part of a circumferential or elliptical curve on a surface of the intraoral scanner.

58. A 3D scanner system according to item 57, wherein the circumferential or elliptical curve forms a closed loop around the intraoral scanner.

59. A 3D scanner system according to any of the items 56-58, wherein the illumination unit comprises a plurality of light sources, such as LEDs.

60. A 3D scanner system according to any of the items 56-59, wherein a first part of the illumination unit is configured for displaying information related to a lower arch of the patient, and wherein a second part of the illumination unit is configured for displaying information related to an upper arch of the patient.

61. A 3D scanner system according to item 60, wherein a first subset of the light sources constitutes the first part of the illumination unit, and wherein a second subset of the light sources constitutes the second part of the illumination unit.

62. A 3D scanner system according to any of the items 60-61, wherein the first part of the illumination unit is lit when scanning the lower arch, and wherein the second part of the illumination unit is lit when scanning the upper arch.

63. A 3D scanner system according to any of the items 60-62, wherein the circumferential or elliptical curve forms a closed loop around the intraoral scanner.

64. A 3D scanner system according to item 63, wherein the first part covers approximately half of the closed loop, and wherein the second part covers approximately the other half of the closed loop.

65. A 3D scanner system according to any of the items 59-64, wherein the brightness and/or color of the light sources is correlated with the generated 3D scan data, such that the illumination unit is configured to visualize the scan coverage, i.e. which parts of the dental arch(es) have been scanned.

66. A 3D scanner system according to any of the items 59-65, wherein the light sources correspond to predefined parts of the dental arches, or wherein each light source corresponds to a dental object in the upper and/or lower arch.

67. A 3D scanner system according to any of the items 59-66, wherein the illumination unit is configured such that a first color of the light sources indicates that the generated 3D scan data is sufficient, and wherein a second color of the light sources indicates that the generated 3D scan data is insufficient.

68. A 3D scanner system according to any of the preceding items, wherein the intraoral scanner further comprises one or more illumination symbols, wherein the brightness and/or color of the illumination symbol(s) is correlated with the generation of 3D scan data.

69. A 3D scanner system according to item 68, wherein the illumination symbol(s) are lit when 3D scan data is being generated during the scanning session.

70. A 3D scanner system according to any of the items 68-69, wherein the intraoral scanner comprises two illumination symbols located on opposite sides of the scanner, wherein a first illumination symbol is lit when scanning an upper arch, and wherein a second illumination symbol is lit when scanning a lower arch.

71. A 3D scanner system according to any of the preceding items, wherein the scanner system comprises a first and a second interaction device, each of said interaction devices configured for initiating an action upon activation.

72. A 3D scanner system according to any of the preceding items, wherein the scanner system comprises a first interaction device and a second interaction device, wherein both of the interaction devices are located on the intraoral scanner.

73. A 3D scanner system according to any of the items 71-72, wherein the first and second interaction devices are located on opposite sides of the intraoral scanner.

74. A 3D scanner system according to any of the items 71-73, wherein the intraoral scanner further comprises a gyroscope configured to determine the orientation of the scanner.

75. A 3D scanner system according to item 74, wherein the first and second interaction devices are interactively coupled to the gyroscope such that only one of said interaction devices is active at any given orientation of the scanner.

76. A 3D scanner system according to any of the items 71-75, wherein the first interaction device is configured to be active at a predefined first interval of orientations of the scanner, and wherein the first interaction device is configured to be inactive if the orientation of the scanner is outside the first interval.

77. A 3D scanner system according to any of the items 71-76, wherein the second interaction device is configured to be active at a predefined second interval of orientations of the scanner, and wherein the second interaction device is configured to be inactive if the orientation of the scanner is outside the second interval.

78. A 3D scanner system according to any of the items 71-77, wherein the intraoral scanner further comprises one or more light sources configured to indicate which of the first or second interaction device is active.

79. A 3D scanner system according to any of the items 71-78, wherein each of the first and second interaction devices is provided with a light source, such as an illumination ring, configured to indicate whether the given interaction device is active or inactive.

80. A 3D scanner system according to any of the preceding items, wherein the intraoral scanner comprises one or more reconfigurable buttons.

81. A 3D scanner system according to item 80, wherein the reconfigurable buttons are based on strain gauge technology or force touch technology.

82. A 3D scanner system according to any of the items 80-81, wherein each reconfigurable button comprises a strain gauge sensor.

83. A 3D scanner system according to item 82, wherein the scanner comprises a display covering the strain gauge sensors.

84. A 3D scanner system according to any of the items 80-82, wherein one or more strain gauge sensors are arranged on a printed circuit board (PCB).

85. A 3D scanner system according to item 84, wherein the PCB is attached to a front layer.

86. A 3D scanner system according to item 85, wherein an electronic display constitutes the front layer.

87. A 3D scanner system according to item 86, wherein the electronic display is configured to display an icon, text, or animation, associated with each strain gauge sensor.

88. A 3D scanner system according to any of the items 86-87, wherein the electronic display is configured to change the icon, text, or animation, based on a progress or a specific step of the scan workflow.

89. A 3D scanner system according to any of the items 86-88, wherein the electronic display is configured to change the icon, text, or animation, associated with a given reconfigurable button based on a user selection among the icons and/or based on a progress or step of the scanning session and/or based on reconfiguring the button associated with the icon.

90. A 3D scanner system according to any of the items 86-88, wherein the scanner system is configured to automatically change the associated action of a given reconfigurable button depending on the scan workflow, and wherein the icon, text, or animation, in the electronic display automatically changes accordingly.

91. A 3D scanner system according to any of the items 80-90, wherein the scanner is configured to change an associated action of the reconfigurable button(s) based on a user selection among the icons and/or based on a progress or step of the scanning session.

92. A 3D scanner system according to any of the items 80-91, wherein the scanner is configured to reconfigure the reconfigurable buttons into a new purpose depending on the progress or step of the scanning session and/or depending on a user activation of one of the reconfigurable buttons.

Although some embodiments have been described and shown in detail, the disclosure is not restricted to such details, but may also be embodied in other ways within the scope of the subject matter defined in the following claims. In particular, it is to be understood that other embodiments may be utilized and structural and functional modifications may be made without departing from the scope of the present disclosure. Furthermore, the skilled person would find it apparent that unless an embodiment is specifically presented only as an alternative, different disclosed embodiments may be combined to achieve a specific implementation and such specific implementation is within the scope of the disclosure.

It should be emphasized that the term "comprises/comprising/including" when used in this specification is taken to specify the presence of stated features, integers, operations, steps or components but does not preclude the presence or addition of one or more other features, integers, steps, components or groups thereof.

In claims enumerating several means, several of these means can be embodied by one and the same item of hardware. The mere fact that certain measures are recited in mutually different dependent claims or described in different embodiments does not indicate that a combination of these measures cannot be used to advantage.

REFERENCE NUMERALS

1. Intraoral scanner
2. Reconfigurable buttons
3. Strain gauge sensor
4. Display
5. Icon
6. Illumination ring
7. Illumination unit
8. Interaction device
9. First interaction device
10. Second interaction device
11. Touch sensitive area(s)
12. Sound
13. Illumination symbol
14. Feedback light source
15. Printed circuit board (PCB)/Carrier
16. Dental arch
17. Data transfer
18. Computer system
19. Intermediate layer/elastic layer

The invention claimed is:

1. A 3D scanner system for scanning a dental arch inside an oral cavity of a patient during a scanning session, the scanner system comprising:
    an intraoral scanner comprising:
        one or more reconfigurable buttons, wherein each reconfigurable button comprises a force sensor;
        a display configured for displaying one or more icons, texts, or animations, associated with the reconfigurable buttons, wherein the display covers the force sensors; and
    one or more processors configured to generate 3D scan data of at least a part of the dental arch.

2. A 3D scanner system according to claim 1, wherein the scanner is configured to change an associated action of the reconfigurable button(s) based on a user selection among the icons or texts and/or based on a progress or step of the scanning session.

3. A 3D scanner system according to claim 1, wherein the display is configured to change the icon, text, or animation, associated with a given reconfigurable button based on a user selection among the icons and/or based on a progress or step of the scanning session.

4. A 3D scanner system according to claim 1, wherein the display is configured to display a visualization of the dental arch, and wherein the scanner system is configured to continuously generate and/or expand the visualization of the dental arch during the scanning session based on the scanned parts of the dental arch.

5. A 3D scanner system according to claim 1, wherein the one or more processors are configured for determining a local scan coverage measure based on whether a given dental object in the dental arch is sufficiently covered by the generated 3D scan data.

6. A 3D scanner system according to claim 5, wherein the local scan coverage measure is based on the density of the generated 3D scan data, such as the density of one or more point clouds.

7. A 3D scanner system according to claim 5, wherein the scanner is configured to color the visualization using a color gradient correlated with the local scan coverage measure, such that part(s) which have been scanned are colored differently than part(s) for which no or insufficient 3D scan data has been generated during the scanning session.

8. A 3D scanner system according to claim 1, wherein the dental arch comprises one or more dental objects, and wherein the display is configured to visualize the dental objects as individual symbols in the visualization of the dental arch.

9. A 3D scanner system according to claim 8, wherein the display is configured to schematically visualize each dental object in the dental arch using five connected surfaces corresponding to the occlusal, buccal, lingual, mesial, and distal surfaces of a tooth.

10. A 3D scanner system according to claim 1, wherein the intraoral scanner further comprises an illumination unit which is integrated in the intraoral scanner, wherein the illumination unit is configured to provide illumination along at least a part of a circumferential or elliptical curve on a surface of the intraoral scanner.

11. A 3D scanner system according to claim 10, wherein the illumination unit comprises a plurality of light sources, and wherein a first subset of the light sources constitutes a first part of the illumination unit, and wherein a second subset of the light sources constitutes a second part of the illumination unit.

12. A 3D scanner system according to claim 11, wherein the first part is lit when scanning a lower arch, and wherein the second part is lit when scanning an upper arch.

13. A 3D scanner system according to claim 11, wherein the brightness and/or color of the light sources is correlated with the local scan coverage measure, such that the illumination unit is configured to visualize the scan coverage, i.e. which parts of the dental arch(es) have been scanned.

14. A 3D scanner system according to claim 1, wherein the intraoral scanner further comprises a feedback light source configured to change illumination, brightness and/or color, when the local scan coverage measure reaches a predefined threshold value, such that the intraoral scanner signals whether enough 3D scan data has been obtained for a given dental object.

15. A 3D scanner system according to claim 1, wherein the intraoral scanner further comprises a touch sensitive ring comprising two or more touch sensitive areas configured for detecting an input from a user, wherein the touch sensitive ring is based on force touch technology.

16. A 3D scanner system according to claim 15, wherein the touch sensitive ring comprises four or more touch sensitive areas, wherein the intraoral scanner further comprises an illumination ring, which is located along the circumference of the touch sensitive ring, wherein the brightness and/or color of the illumination ring is correlated with the local scan coverage measure.

17. A 3D scanner system according to claim 15, wherein the intraoral scanner further comprises an illumination ring, which is located along the circumference of the touch sensitive ring, wherein the brightness and/or color of the illumination ring is correlated with the local scan coverage measure.

18. A 3D scanner system according to claim 1, wherein the display is configured to display an icon associated with each force sensor.

19. A 3D scanner system according to claim 1, wherein the scanner system is configured to reconfigure the reconfigurable buttons into a new purpose depending on the progress or step of the scanning session and/or depending on a user activation of one of the reconfigurable buttons.

20. A 3D scanner system according to claim 1, wherein the force sensors are selected from the group of: strain-gauge based force sensors, MEMS piezoresistive sensors, MEMS capacitive pressure sensors, optical pressure sensors, flexible thin-film force sensors, or piezoelectric force sensors.

\* \* \* \* \*